United States Patent
Pandya et al.

(10) Patent No.: US 9,707,218 B2
(45) Date of Patent: Jul. 18, 2017

(54) DERIVATIVES OF PYRAZOLE-SUBSTITUTED AMINO-HETEROARYL COMPOUNDS

(71) Applicant: Concert Pharmaceuticals, Inc., Lexington, MA (US)

(72) Inventors: Bhaumik A. Pandya, Arlington, MA (US); Craig E. Masse, Cambridge, MA (US); Ian Robert Silverman, Arlington, MA (US); Roger D. Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 14/840,952

(22) Filed: Aug. 31, 2015

(65) Prior Publication Data
US 2015/0366853 A1    Dec. 24, 2015

Related U.S. Application Data

(63) Continuation of application No. 14/016,791, filed on Sep. 3, 2013, now Pat. No. 9,145,390, which is a continuation of application No. PCT/US2012/027341, filed on Mar. 1, 2012.

(60) Provisional application No. 61/448,887, filed on Mar. 3, 2011, provisional application No. 61/697,091, filed on Sep. 5, 2012.

(51) Int. Cl.
| | |
|---|---|
| A61K 31/454 | (2006.01) |
| A61K 31/4545 | (2006.01) |
| C07D 401/14 | (2006.01) |
| A61K 45/06 | (2006.01) |
| A61K 31/44 | (2006.01) |
| A61K 31/517 | (2006.01) |

(52) U.S. Cl.
CPC .......... *A61K 31/4545* (2013.01); *A61K 31/44* (2013.01); *A61K 31/517* (2013.01); *A61K 45/06* (2013.01); *C07D 401/14* (2013.01)

(58) Field of Classification Search
CPC .......................... A61K 31/454; A61K 31/4545
USPC .......................................................... 514/318
See application file for complete search history.

(56) References Cited

U.S. PATENT DOCUMENTS

| | | | |
|---|---|---|---|
| 6,221,335 B1 | 4/2001 | Foster | |
| 6,334,997 B1 | 1/2002 | Foster et al. | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 7,825,137 B2 | 11/2010 | Christensen et al. | |
| 8,343,950 B2 | 1/2013 | Tung | |
| 2006/0046991 A1 | 3/2006 | Cui et al. | |
| 2007/0082929 A1 | 4/2007 | Gant et al. | |
| 2007/0197695 A1 | 8/2007 | Potyen et al. | |
| 2008/0021019 A1 | 1/2008 | Chan et al. | |
| 2008/0103122 A1 | 5/2008 | Veltri | |
| 2009/0269354 A1 | 10/2009 | Masse et al. | |
| 2010/0324061 A1 | 12/2010 | Cui et al. | |
| 2011/0003805 A1 | 1/2011 | Ohta et al. | |
| 2014/0005211 A1 | 1/2014 | Pandya et al. | |

FOREIGN PATENT DOCUMENTS

| | | |
|---|---|---|
| CN | 101836991 | 9/2010 |
| CN | 101967140 | 2/2011 |
| WO | WO 95/26325 | 10/1995 |
| WO | WO 2004/076412 | 9/2004 |
| WO | WO 2006/021881 | 3/2006 |
| WO | WO 2006/021884 | 3/2006 |

(Continued)

OTHER PUBLICATIONS

Chambers et al., Dissemination and Growth of Cancer Cells in Metastatic Sites, Nature Reviews, vol. 2, pp. 663-672 (2002).*

(Continued)

*Primary Examiner* — Patricia L Morris
(74) *Attorney, Agent, or Firm* — Fish & Richardson P.C.

(57) ABSTRACT

This invention relates to novel pyrazole-substituted amino-heteroaryl compounds of Formula I:

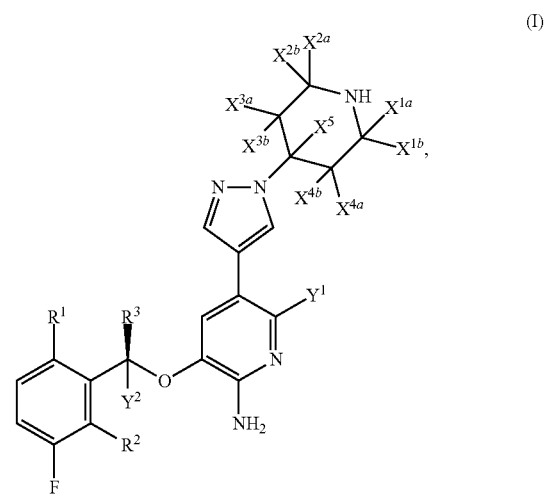

and pharmaceutically acceptable salts thereof. This invention also provides compositions comprising a compound of this invention and the use of such compositions in methods of treating diseases and conditions that are beneficially treated by administering an inhibitor of anaplastic lymphoma kinase (ALK).

8 Claims, 3 Drawing Sheets

(56) References Cited

FOREIGN PATENT DOCUMENTS

| WO | WO 2007/118651 | 10/2007 |
|---|---|---|
| WO | WO 2010/019701 | 2/2010 |
| WO | WO 2010/108103 | 9/2010 |

OTHER PUBLICATIONS

Wells et al., The dormancy dilemma: Quiescence versus balanced proliferation, Cancer Res. 73(13), pp. 1-10 (2013).*
Pearce et al., Failure modes in anticancer drug discovery and development, Cancer Drug Design and Discovery Edited by Stephen Neidle, Chapter 18, pp. 424-435 (2008).*
Bone Cancer, American Cancer Society, 42 pages (2014).*
LeRoith et al., The insulin-like growth factor system and cancer, Cancer Letters, 195, pp. 127-137 (2003).*
Simone, Oncology:Introduction, Cecil Textbook of Medicine, ed Bennett et al. W.B.Saunders Co. 20th ed, vol. 1, 1996, pp. 1004-1010.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Lodish et al., "Endocrine side, etc.," Endocrine-Related Cancer (2010) 17, R233-R244.*
Lodish et al., "Endocrine side, etc.," Endocrine-Related Cancer (2010) 17, R233-R244.Lodish et al., "Endocrine side, etc.," Endocrine-Related Cancer (2010) 17, R233-R244.*
Ouaissi et al., "Rationale for Possible, etc.," Journal of Biomedicine and Biotechnology, 2011, Article: ID 315939, 1-8.*
International Search Report and Written Opinion in International Application No. PCT/US12/27341, mailed Jun. 6, 2012, 12 pages.
International Preliminary Report on Patentability in International Application No. PCT/US/12/27341, mailed Mar. 12, 2014, 8 pages.
International Search Report and Written Opinion in International Application No. PCT/US213/070983, mailed Apr. 1, 2014, 17 pages.
International Preliminary Report on Patentability in International Application No. PCT/US2013/070983, mailed May 26, 2015, 9 pages.
Quinidine, Drugs @ FDA, FDA Approved Drug Products, retrieved May 29, 2014, http://www.accessdata.fda.gov/scripts/cder/drugsatfda/index.cfm?fuseaction=Search.SearchAction &SearchType=BasicSearch&searchTerm=quinidine&Search_Button=Submit, 2 pages.
Baillie, "The Use of Stable Isotopes in Pharmacological Research," Pharmacology Rev, 1981, 33(2):81-132.
Blake et al., "Studies with Deuterated Drugs," J Pharm Sci, 1975, 64:367-391.
Browne, "Stable Isotope Techniques in Early Drug Development: An Economic Evaluation," J. Clin. Pharmacology, 1998, 38: 213-20.
Cherrah et al., "Study of Deuterium Isotope Effects on Protein Binding by Gas Chromatography/Mass Spectrometry. Caffeine and Deuterated Isotopomers," Biomed. and Environmental Mass Spectrometry, 1987, 14: 653-57.

Dyck et al., "Effects of Deuterium Substitution on the Catabolism of ?-Phenylethylamine: An In Vivo Study," J. Neurochemistry, 1986, 46: 399-404.
Fisher et al., "The complexities inherent in attempts to decrease drug clearance by blocking sites of CYP-mediated metabolism," Curr. Opin. Drug Discov. Dev., 2006, 9(1):101-109.
Foster, "Deuterium isotope effects in studies of drug metabolism," Trends in Pharmaceutical Sciences, 1984, 524-527.
Foster, "Deuterium Isotope Effects in the Metabolism of Drugs and Xenobiotics: Implications for Drug Design," Adv. Drug Res., 1985, 14: 2-40.
Fukuto et al., "Determination of the Mechanism of Demthylenation of (Methylenedioxy)phenyl Compounds by Cytochrome P450 Using Deuterium Isotope Effects," J Med Chem, 1991, 34:2871-2876.
Gouyette, "Synthesis of Deuterium-labelled Elliptinium and its Use in Metabolic Studies," Biomed. and Environmental Mass Spectrometry, 1988, 15: 243-47.
Haskins, "The Application of Stable Isotopes in Biomedical Research," Biomed. Spectrometry, 1982, 9(7):269-77.
Hesk and McNamara, "Synthesis of isotopically labelled compounds at Schering-Plough, an historical perspective," J. Labelled Compounds and Radiopharm, 2007, 50:131-137.
Honma et al., "The Metabolism of Roxatidine Acetate Hydrochloride," Drug Metab. Dispos, 1987, 15(4): 551-559.
Koning et al., "Fit-for-Purpose Development of the Enabling route to Crizotinib (PF-02341066)," Org Res Process Dev, 2011, 15:1018-1026.
Kushner et al. "Pharmacological uses and perspectives of heavy water and deuterated compounds," Can. J. Physiol. Pharmacol. 1999, 77: 79-88.
O'Donnell, "Discovery of 4-(5-methyloxazolo[4,5-b]pyridin-2-yl)-1,4-diazabicyclo[3.2.2]nonane (CP-810,123), a novel alpha 7 nicotinic acetylcholine receptor agonist for the treatment of cognitive disorders in schizophrenia: synthesis, SAR development, and in vivo efficacy in cognition models," J Med Chem, 2010, 53:1222-1237.
Pieniaszek et al., "Moricizine bioavailability via simultaneous, dual, stable isotope administrations: bioequivalence," J. Clin. Pharmacology, 1999, 39:817-25.
Sasaki et al., "The Biology and Treatment of EML4-ALK Non-Small Cell Lung Cancer," Eur J Cancer, Jul. 2010, 46(10):1773-1780.
Shimizu, "Negishi coupling strategy of a repetitive two-step method for oligoarene synthesis," Tetrahedron Letters, 2006, 47:5927-5931.
Tonn et al., "Simultaneous Analysis of Diphenhydramine and a Stable Isotope Analog ($^2$H10) Diphenhydramine Using Capillary Gas Chromatography with Mass Selective Detection in Biological Fluids from Chronically Instrumented Pregnant Ewes," Biol. Mass Spectrometry, 1993, 22:633-642.
Wolen, "The Application of Stable Isotopes to Studies of Drug Bioavailability and Bioequivalence," J. Clin. Pharmacology, 1986, 26:419-424.
Xalkori (crixotinib) Prescribing Information, www.fda.gov, Feb. 2012, 14 pages.
Wu et al., English Translation of CN 101967140, Feb. 9, 2011.

* cited by examiner

DERIVATIVES OF PYRAZOLE-SUBSTITUTED AMINO-HETEROARYL COMPOUNDS

CROSS-REFERENCE TO RELATED APPLICATIONS

This application is a continuation of application Ser. No. 14/016,791, filed Sep. 3, 2013, which is a continuation of International Application number PCT/US2012/027341, filed Mar. 1, 2012, which claims the benefit of U.S. Provisional Application No. 61/448,887, filed Mar. 3, 2011, and which Ser. No. 14/016,791 Application further claims the benefit of U.S. Provisional Application No. 61/697,091, filed Sep. 5, 2012. The disclosures of the prior applications are considered part of (and are incorporated by reference in) the disclosure of this application.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

Crizotinib also known as 3-[1(R)-(2,6-dichloro-3-fluorophenyl)ethoxy]-5-[1-(4-piperidinyl)-1H-pyrazol-4-yl]pyridin-2-amine is known to inhibit hepatocyte growth factor receptor (c-met/HGFR) kinase and also to block the tyrosine kinase of anaplastic lympohoma kinase (ALK). A percentage of non-small cell lung cancer patients carry the echinoderm microtubule-associated protein-like 4 anaplastic lymphoma kinase (EML4-ALK) fusion gene. EML4-ALK, when inserted into a normal cell, causes the cell to become cancerous. Crizotinib blocks the tyrosine kinase of the ALK domain of this fusion gene. See Sasaki, t et al., The Biology and Treatment of EML4-ALK Non-Small Cell Lung Cancer, Eur. J. Cancer, 2010, July; 46(10): 1773-80.

Crizotinib currently is recommended for approval for non-small cell lung cancer (NSCLC) and is undergoing Phase I/II clinical trials for solid tumor cancer and for lymphoma.

Treatment with crizotinib has been associated with mild to moderate gastrointestinal-related events and fatigue.

Despite the beneficial activities of crizotinib, there is a continuing need for new compounds to treat the aforementioned diseases and conditions.

SUMMARY OF THE INVENTION

This invention relates to novel pyrazole-substituted amino-heteroaryl compounds, and pharmaceutically acceptable salts thereof. This invention also provides compositions comprising a compound of this invention and the use of such compositions in methods of treating diseases and conditions that are beneficially treated by administering an inhibitor of anaplastic lymphoma kinase (ALK) and hepatocyte growth factor receptor (c-met/HGFR) kinase.

DEFINITIONS

Figure 1A:
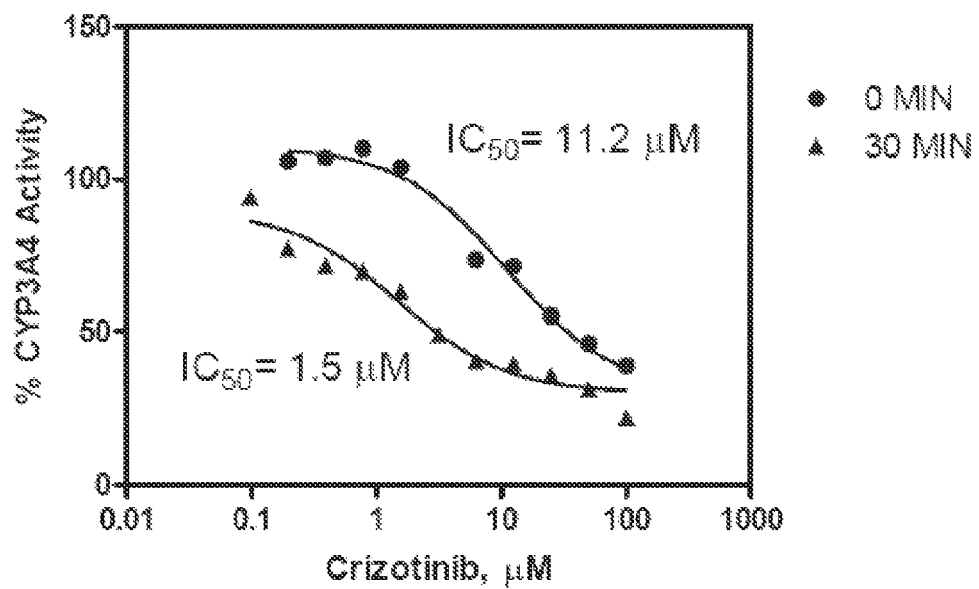
FIG. 1A shows $IC_{50}$ shift assessment plots for crizotinib.

The term "treat" means decrease, suppress, attenuate, diminish, arrest, or stabilize the development or progression of a disease (e.g., a disease or disorder delineated herein), lessen the severity of the disease or improve or lessen the severity of one or more symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of crizotinib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, a salt of a provided compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

Unless otherwise indicated, when a disclosed compound is named or depicted by a structure without specifying the stereochemistry and has one or more chiral centers, it is understood to represent all possible stereoisomers of the compound.

The term "subject" as used herein includes a human or a non-human animal, such as mouse, rat, guinea pig, dog, cat, horse, cow, pig, monkey (e.g., rhesus), chimpanzee, or baboon. In one embodiment, the subject is a non-human animal. In another embodiment, the subject is a human.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual stereoisomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

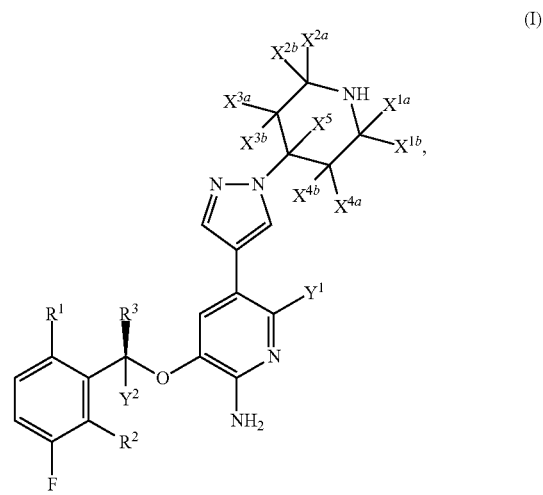

or a pharmaceutically acceptable salt thereof, wherein:

$R^1$ and $R^2$ are each independently selected from Cl, $CH_3$ and $CD_3$;

$R^3$ is $CH_3$ or $CD_3$;

$X^{1a}$, $X^{1b}$, $X^{2a}$, $X^{2b}$, $X^{3a}$, $X^{3b}$, $X^{4a}$, $X^{4b}$, and $X^5$ are each independently selected from hydrogen and deuterium;

$Y^1$ is hydrogen or deuterium; and $Y^2$ is hydrogen or deuterium;

provided that when each of $R^1$ and $R^2$ are Cl, each of $X^{1a}$, $X^{1b}$, $X^{2a}$, $X^{2b}$, $X^{3a}$, $X^{3b}$, $X^{4a}$, $X^{4b}$, and $X^5$ is hydrogen and each of $Y^1$ and $Y^2$ is hydrogen, then $R^3$ is $CD_3$.

In one embodiment of the compound of formula I, when each of $R^1$ and $R^2$ are Cl, each of $X^{1a}$, $X^{1b}$, $X^{2a}$, $X^{2b}$, $X^{3a}$, $X^{3b}$, $X^{4a}$, $X^{4b}$, and $X^5$ is hydrogen and $Y^1$ is hydrogen, then $R^3$ is $CD_3$.

In one embodiment of the compound of formula I, when each of $R^1$ and $R^2$ are Cl, each of $X^{1a}$, $X^{1b}$, $X^{2a}$, $X^{2b}$, $X^{3a}$, $X^{3b}$, $X^{4a}$, and $X^{4b}$ is hydrogen and each of $Y^1$ and $Y^2$ is hydrogen, then $R^3$ is $CD_3$.

In one embodiment of the compound of formula I, when $R^1$ and $R^2$ are each Cl, each of $X^{1a}$, $X^{1b}$, $X^{2a}$, $X^{2b}$, $X^{3a}$, $X^{3b}$, $X^{4a}$, and $X^{4b}$ is hydrogen, $Y^1$ is hydrogen, and $X^5$ is deuterium, then $R^3$ is $CD_3$.

In one embodiment of the compound of formula I, when $R^1$ and $R^2$ are each Cl, each of $X^{1a}$, $X^{1b}$, $X^{2a}$, $X^{2b}$, $X^{3a}$, $X^{3b}$, $X^{4a}$, and $X^{4b}$ is hydrogen, $Y^1$ is hydrogen, and $Y^2$ is deuterium, then $R^3$ is $CD_3$.

In one embodiment of the compound of formula I, when $R^1$ and $R^2$ are each Cl, each of $X^{1a}$, $X^{1b}$, $X^{2a}$, $X^{2b}$, $X^{3a}$, $X^{3b}$, $X^{4a}$, and $X^{4b}$ is hydrogen, $Y^1$ is hydrogen, and $X^5$ and $Y^2$ are each deuterium, then $R^3$ is $CD_3$.

In one embodiment of the compound of Formula I, when $R^1$ and $R^2$ are each independently selected from Cl and $CH_3$, and $X^{1a}$, $X^{1b}$, $X^{2a}$, $X^{2b}$, $X^{3a}$, $X^{3b}$, $X^{4a}$, $X^{4b}$, and $X^5$ is hydrogen and each of $Y^1$ and $Y^2$ is hydrogen, then $R^3$ is $CD_3$.

In one embodiment of a compound of Formula I, $X^{1a}$ and $X^{1b}$ are the same, $X^{2a}$ and $X^{2b}$ are the same, $X^{3a}$ and $X^{3b}$ are the same, and $X^{4a}$ and $X^{4b}$ are the same. In one aspect of this embodiment $R^1$ and $R^2$ are independently selected from Cl and $CD_3$. In a further aspect of this embodiment, $R^1$ and $R^2$ are the same and are each Cl. In another further aspect of this embodiment, $R^1$ and $R^2$ are the same and are each $CD_3$.

In one embodiment of a compound of Formula I, $X^{1a}$, $X^{1b}$, $X^{2a}$ and $X^{2b}$ are the same, $X^{3a}$, $X^{3b}$, $X^{4a}$ and $X^{4b}$ are the same and $R^1$ and $R^2$ are independently selected from Cl and $CD_3$. In one aspect, each of $X^{1a}$, $X^{1b}$, $X^{2a}$ and $X^{2b}$ is hydrogen; and each of $X^{3a}$, $X^{3b}$, $X^{4a}$ and $X^{4b}$ is deuterium. In one aspect, each of $X^{1a}$, $X^{1b}$, $X^{2a}$ and $X^{2b}$ is deuterium; and each of $X^{3a}$, $X^{3b}$, $X^{4a}$ and $X^{4b}$ is hydrogen. In one aspect, each of $X^{1a}$, $X^{1b}$, $X^{2a}$, $X^{2b}$, $X^{3a}$, $X^{3b}$, $X^{4a}$ and $X^{4b}$ is deuterium. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect of this embodiment, $R^1$ and $R^2$ are the same and are each Cl. In one aspect of this embodiment, $R^1$ and $R^2$ are the same and are each $CD_3$.

In one embodiment of a compound of Formula I, each of $X^{1a}$, $X^{1b}$, $X^{2a}$, $X^{2b}$, $X^{3a}$, $X^{3b}$, $X^{4a}$ and $X^{4b}$ is hydrogen, $R^1$ and $R^2$ are the same and are selected from Cl and $CD_3$ and $R^3$ is $CH_3$. In one aspect, $R^1$ and $R^2$ are each Cl. In one aspect, $R^1$ and $R^2$ are each $CD_3$.

In one embodiment of a compound of Formula I, each of $X^{1a}$, $X^{1b}$, $X^{2a}$, $X^{2b}$, $X^{3a}$, $X^{3b}$, $X^{4a}$ and $X^{4b}$ is hydrogen, $R^1$ and $R^2$ are the same and are selected from Cl and $CD_3$ and $R^3$ is $CD_3$. In one aspect, $R^1$ and $R^2$ are each Cl. In one aspect, $R^1$ and $R^2$ are each $CD_3$.

In one embodiment of a compound of Formula I, each of $X^{1a}$, $X^{1b}$, $X^{2a}$, $X^{2b}$, $X^{3a}$, $X^{3b}$, $X^{4a}$ and $X^{4b}$ is deuterium, $R^1$ and $R^2$ are the same and are selected from Cl and $CD_3$ and $R^3$ is $CH_3$. In one aspect, $R^1$ and $R^2$ are each Cl. In one aspect, $R^1$ and $R^2$ are each $CD_3$.

In one embodiment of a compound of Formula I, each of $X^{1a}$, $X^{1b}$, $X^{2a}$, $X^{2b}$, $X^{3a}$, $X^{3b}$, $X^{4a}$ and $X^{4b}$ is deuterium; $R^1$ and $R^2$ are the same and are selected from Cl and $CD_3$ and $R^3$ is $CD_3$. In one aspect, $R^1$ and $R^2$ are each Cl. In one aspect, $R^1$ and $R^2$ are each $CD_3$.

In one embodiment of a compound of Formula I, each of $X^{1a}$, $X^{1b}$, $X^{2a}$ and $X^{2b}$ is deuterium, each of $X^{3a}$, $X^{3b}$, $X^{4a}$ and $X^{4b}$ is hydrogen, $R^1$ and $R^2$ are the same and are selected from Cl and $CD_3$ and $R^3$ is $CH_3$. In one aspect, $R^1$ and $R^2$ are each Cl. In one aspect, $R^1$ and $R^2$ are each $CD_3$.

In one embodiment of a compound of Formula I, each of $X^{1a}$, $X^{1b}$, $X^{2a}$ and $X^{2b}$ is deuterium, each of $X^{3a}$, $X^{3b}$, $X^{4a}$ and $X^{4b}$ is hydrogen, $R^1$ and $R^2$ are the same and are selected from Cl and $CD_3$ and $R^3$ is $CD_3$. In one aspect, $R^1$ and $R^2$ are each Cl. In one aspect, $R^1$ and $R^2$ are each $CD_3$.

In one embodiment of a compound of Formula I, each of $X^{1a}$, $X^{1b}$, $X^{2a}$ and $X^{2b}$ is hydrogen, each of $X^{3a}$, $X^{3b}$, $X^{4a}$ and $X^{4b}$ is deuterium, $R^1$ and $R^2$ are the same and are selected from Cl and $CD_3$ and $R^3$ is $CH_3$. In one aspect, $R^1$ and $R^2$ are each Cl. In one aspect, $R^1$ and $R^2$ are each $CD_3$.

In one embodiment of a compound of Formula I, each of $X^{1a}$, $X^{1b}$, $X^{2a}$ and $X^{2b}$ is hydrogen, each of $X^{3a}$, $X^{3b}$, $X^{4a}$ and $X^{4b}$ is deuterium, $R^1$ and $R^2$ are the same and are selected from Cl and $CD_3$ and $R^3$ is $CD_3$. In one aspect, $R^1$ and $R^2$ are each Cl. In one aspect, $R^1$ and $R^2$ are each $CD_3$.

In one embodiment of a compound of Formula I, $X^5$ is hydrogen, $Y^1$ is hydrogen, $Y^2$ is hydrogen and $R^1$ and $R^2$ are the same and are selected from Cl and $CD_3$. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect each of $X^{1a}$, $X^{1b}$, $X^{2a}$, $X^{2b}$, $X^{3a}$, $X^{3b}$, $X^{4a}$ and $X^{4b}$ is deuterium. In an exaxmple of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is hydrogen and each of $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is deuterium and each of $X^{3a}$, $X^{3b}$, $X^{4a}$ and $X^{4b}$ is hydrogen. In an example of this aspect $R^3$ is $CH_3$. In another example of this aspect $R^3$ is $CD_3$. In an example of this aspect $Y^2$ is hydrogen. In another example of this aspect $Y^2$ is deuterium.

In one embodiment of a compound of Formula I, $X^5$ is hydrogen, $Y^1$ is deuterium, $Y^2$ is hydrogen and $R^1$ and $R^2$ are the same and are selected from Cl and $CD_3$. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect each of $X^{1a}$, $X^{1b}$, $X^{2a}$, $X^{2b}$, $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is hydrogen and each of $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is deuterium and each of $X^{3a}$, $X^{3b}$, $X^{4a}$ and $X^{4b}$ is hydrogen. In an example of this aspect $R^3$ is $CH_3$. In another example of this aspect $R^3$ is $CD_3$. In an example of this aspect $Y^2$ is hydrogen. In another example of this aspect $Y^2$ is deuterium.

In one embodiment of a compound of Formula I, $X^5$ is hydrogen, $Y^1$ is hydrogen, $Y^2$ is deuterium and $R^1$ and $R^2$ are the same and are selected from Cl and $CD_3$. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect each of $X^{1a}$, $X^{1b}$, $X^{2a}$, $X^{2b}$, $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is hydrogen and each of $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is deuterium and each of $X^{3a}$, $X^{3b}$, $X^{4a}$ and $X^{4b}$ is hydrogen. In an example of this aspect $R^3$ is $CH_3$. In another example of this aspect $R^3$ is $CD_3$. In an example of this aspect $Y^2$ is hydrogen. In another example of this aspect $Y^2$ is deuterium.

In one embodiment of a compound of Formula I, $X^5$ is hydrogen, $Y^1$ is deuterium, $Y^2$ is deuterium and $R^1$ and $R^2$ are the same and are selected from Cl and $CD_3$. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect each of $X^{1a}$, $X^{1b}$, $X^{2a}$, $X^{2b}$, $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is hydrogen and each of $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{11}$, $X^{1b}$, $X^{2a}$ and $X^{2b}$ is deuterium and each of $X^{3a}$, $X^{3b}$, $X^{4a}$ and $X^{4b}$ is hydrogen. In an example of this aspect $R^3$ is $CH_3$. In another example of this aspect $R^3$ is $CD_3$. In an example of this aspect $Y^2$ is hydrogen. In another example of this aspect $Y^2$ is deuterium.

In one embodiment of a compound of Formula I, $X^5$ is deuterium, $Y^1$ is hydrogen, $Y^2$ is hydrogen and $R^1$ and $R^2$ are the same and are selected from Cl and $CD_3$. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect each of $X^{1a}$, $X^{1b}$, $X^{2a}$, $X^{2b}$, $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is hydrogen and each of $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is deuterium and each of $X^{3a}$, $X^{3b}$, $X^{4a}$ and $X^{4b}$ is hydrogen. In an example of this aspect $R^3$ is $CH_3$. In another example of this aspect $R^3$ is $CD_3$. In an example of this aspect $Y^2$ is hydrogen. In another example of this aspect $Y^2$ is deuterium.

In one embodiment of a compound of Formula I, $X^5$ is deuterium, $Y^1$ is deuterium, $Y^2$ is hydrogen and $R^1$ and $R^2$ are the same and are selected from Cl and $CD_3$. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect each of $X^{1a}$, $X^{1b}$, $X^{2a}$, $X^{2b}$, $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is hydrogen and each of $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is deuterium and each of $X^{3a}$, $X^{3b}$, $X^{4a}$ and $X^{4b}$ is hydrogen. In an example of this aspect $R^3$ is $CH_3$. In another example of this aspect $R^3$ is $CD_3$. In an example of this aspect $Y^2$ is hydrogen. In another example of this aspect $Y^2$ is deuterium.

In one embodiment of a compound of Formula I, $X^5$ is deuterium, $Y^1$ is hydrogen, $Y^2$ is deuterium and $R^1$ and $R^2$ are the same and are selected from Cl and $CD_3$. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect each of $X^{1a}$, $X^{1b}$, $X^{2a}$, $X^{2b}$, $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is hydrogen and each of $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is deuterium and each of $X^{3a}$, $X^{3b}$, $X^{4a}$ and $X^{4b}$ is hydrogen. In an example of this aspect $R^3$ is $CH_3$. In another example of this aspect $R^3$ is $CD_3$. In an example of this aspect $Y^2$ is hydrogen. In another example of this aspect $Y^2$ is deuterium.

In one embodiment of a compound of Formula I, $X^5$ is deuterium, $Y^1$ is deuterium, $Y^2$ is deuterium and $R^1$ and $R^2$ are the same and are selected from Cl and $CD_3$. In one aspect, each of $X^{1a}$, $X^{1b}$, $X^{2a}$, $X^{2b}$, $X^{3a}$, $X^{3b}$, $X^{4a}$ and $X^{4b}$ is hydrogen. In one aspect each of $X^{1a}$, $X^{1b}$, $X^{2a}$, $X^{2b}$, $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is hydrogen and each of $X^{3a}$, $X^{3b}$, $X^{4a}$ and $X^{4b}$ is deuterium. In an example of this aspect $R^3$ is $CH_3$. In another example of this aspect $R^3$ is $CD_3$. In an example of this aspect $Y^2$ is hydrogen. In another example of this aspect $Y^2$ is deuterium. In one aspect each of $X^{1a}$, $X^{1b}$, $X^{2a}$ and $X^{2b}$ is deuterium and each of $X^{3a}$, $X^{3b}$, $X^{4a}$ and $X^{4b}$ is hydrogen. In an example of this aspect $R^3$ is $CH_3$. In another example of this aspect $R^3$ is $CD_3$. In an example of this aspect $Y^2$ is hydrogen. In another example of this aspect $Y^2$ is deuterium.

In an example of any of the foregoing embodiments, the compound is a compound of Formula I as defined above wherein any atom not designated as deuterium is present at its natural isotopic abundance.

In one embodiment, the compound is selected from any one of the compounds (Cmpd) set forth in Table 1 (below):

TABLE 1

Compounds of Formula I

| Cmpd | $X^{1a}/X^{1b}$ | $X^{2a}/X^{2b}$ | $X^{3a}/X^{3b}$ | $X^{4a}/X^{4b}$ | $X^5$ | $Y^1$ | $Y^2$ | $R^1$ | $R^2$ | $R^3$ |
|---|---|---|---|---|---|---|---|---|---|---|
| 100 | D | D | D | D | D | D | D | Cl | Cl | $CD_3$ |
| 101 | D | D | D | D | D | H | D | Cl | Cl | $CD_3$ |
| 102 | D | D | D | D | H | D | H | Cl | Cl | $CH_3$ |
| 103 | D | D | H | H | D | H | D | Cl | Cl | $CD_3$ |
| 104 | D | D | H | H | D | H | H | Cl | Cl | $CH_3$ |
| 105 | D | D | H | H | D | D | H | Cl | Cl | $CH_3$ |
| 106 | D | D | H | H | H | D | H | Cl | Cl | $CH_3$ |
| 107 | D | D | H | H | H | D | D | Cl | Cl | $CD_3$ |
| 108 | H | H | D | D | D | D | H | Cl | Cl | $CD_3$ |
| 109 | H | H | D | D | D | H | H | Cl | Cl | $CH_3$ |
| 110 | H | H | D | D | D | H | D | Cl | Cl | $CD_3$ |
| 111 | H | H | D | D | D | D | H | Cl | Cl | $CH_3$ |
| 112 | H | H | H | H | H | H | H | Cl | Cl | $CD_3$ |
| 113 | D | D | D | D | D | D | D | $CD_3$ | $CD_3$ | $CD_3$ |
| 114 | D | D | D | D | D | H | D | $CD_3$ | $CD_3$ | $CD_3$ |
| 115 | D | D | D | D | H | D | H | $CD_3$ | $CD_3$ | $CH_3$ |
| 116 | D | D | H | H | D | H | D | $CD_3$ | $CD_3$ | $CD_3$ |
| 117 | D | D | H | H | D | H | H | $CD_3$ | $CD_3$ | $CH_3$ |
| 118 | D | D | H | H | D | D | H | $CD_3$ | $CD_3$ | $CH_3$ |
| 119 | D | D | H | H | H | D | H | $CD_3$ | $CD_3$ | $CH_3$ |
| 120 | D | D | H | H | H | D | D | $CD_3$ | $CD_3$ | $CD_3$ |
| 121 | H | H | D | D | D | D | H | $CD_3$ | $CD_3$ | $CD_3$ |
| 122 | H | H | D | D | D | H | H | $CD_3$ | $CD_3$ | $CH_3$ |
| 123 | H | H | D | D | D | H | D | $CD_3$ | $CD_3$ | $CD_3$ |
| 124 | H | H | D | D | D | D | H | $CD_3$ | $CD_3$ | $CH_3$ |
| 125 | H | H | H | H | H | H | H | $CD_3$ | $CD_3$ | $CD_3$ | wherein any atom not designated as deuterium is present at its natural isotopic abundance, or a pharmaceutically acceptable salt thereof.

In one embodiment, the compound is selected from any one of the compounds (Cmpd) set forth in Table 2 (below):

TABLE 2

Compounds of Formula I

| Cmpd | $X^{1a}/X^{1b}$ | $X^{2a}/X^{2b}$ | $X^{3a}/X^{3b}$ | $X^{4a}/X^{4b}$ | $X^5$ | $Y^1$ | $Y^2$ | $R^1$ | $R^2$ | $R^3$ |
|---|---|---|---|---|---|---|---|---|---|---|
| 200 | D | D | D | D | D | H | H | Cl | Cl | $CD_3$ |
| 201 | D | D | D | D | D | H | D | Cl | Cl | $CH_3$ |
| 202 | H | H | H | H | H | H | D | Cl | Cl | $CD_3$ |
| 223 | H | H | H | H | H | H | D | Cl | Cl | $CH_3$ | wherein any atom not designated as deuterium is present at its natural isotopic abundance, or a pharmaceutically acceptable salt thereof.

In one embodiment, the compound is selected from any one of the compounds (Cmpd) set forth in Table 3 (below):

TABLE 3

Compounds of Formula I

| Cmpd | $X^{1a}/X^{1b}$ | $X^{2a}/X^{2b}$ | $X^{3a}/X^{3b}$ | $X^{4a}/X^{4b}$ | $X^5$ | $Y^1$ | $Y^2$ | $R^1$ | $R^2$ | $R^3$ |
|---|---|---|---|---|---|---|---|---|---|---|
| 210 | D | D | D | D | H | H | H | Cl | Cl | $CH_3$ |
| 211 | H | H | D | D | H | H | H | Cl | Cl | $CH_3$ |
| 212 | D | D | H | H | H | H | H | Cl | Cl | $CH_3$ |
| 213 | D | D | D | D | H | H | H | Cl | Cl | $CD_3$ |
| 214 | H | H | D | D | H | H | H | Cl | Cl | $CD_3$ |
| 215 | D | D | H | H | H | H | H | Cl | Cl | $CD_3$ |
| 216 | D | D | D | D | H | H | D | Cl | Cl | $CD_3$ |
| 217 | H | H | D | D | H | H | D | Cl | Cl | $CD_3$ |
| 218 | D | D | H | H | H | H | D | Cl | Cl | $CD_3$ |
| 219 | D | D | D | D | D | H | H | Cl | Cl | $CH_3$ |
| 220 | H | H | D | D | D | H | H | Cl | Cl | $CD_3$ |
| 221 | D | D | H | H | D | H | H | Cl | Cl | $CD_3$ |
| 222 | H | H | H | H | D | H | H | Cl | Cl | $CD_3$ |
| 224 | H | H | H | H | D | H | D | Cl | Cl | $CD_3$ | wherein any atom not designated as deuterium is present at its natural isotopic abundance, or a pharmaceutically acceptable salt thereof.

The synthesis of compounds of Formula I may be readily achieved by synthetic chemists of ordinary skill by reference to the Exemplary Synthesis and Examples disclosed herein. Relevant procedures analogous to those of use for the preparation of compounds of Formula I and intermediates thereof are disclosed, for instance in Cui, J., WO 2006/021881, Cui, J. WO 2006/021884, Lui, J. WO 2010/108103, O'Donnell, C. J.; J. Med. Chem. 2010, 53, 1222-1237, and Shimizu, H. Tetrahedron Lett. 2006, 47, 5927-5931.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I is depicted in Scheme 1.

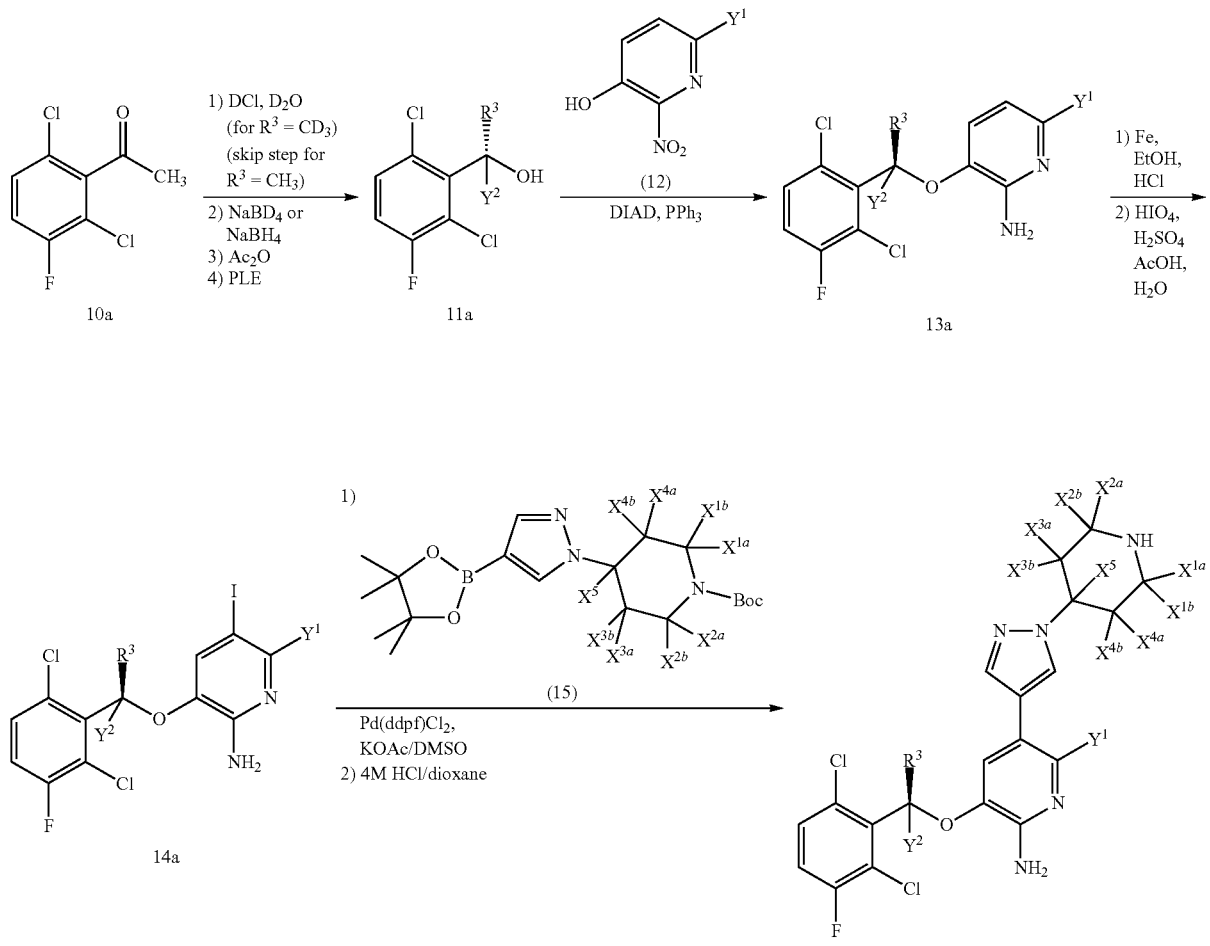

Scheme 1a: Synthetic Route to Compounds of Formula I ($R^1$ and $R^2$ = Cl)

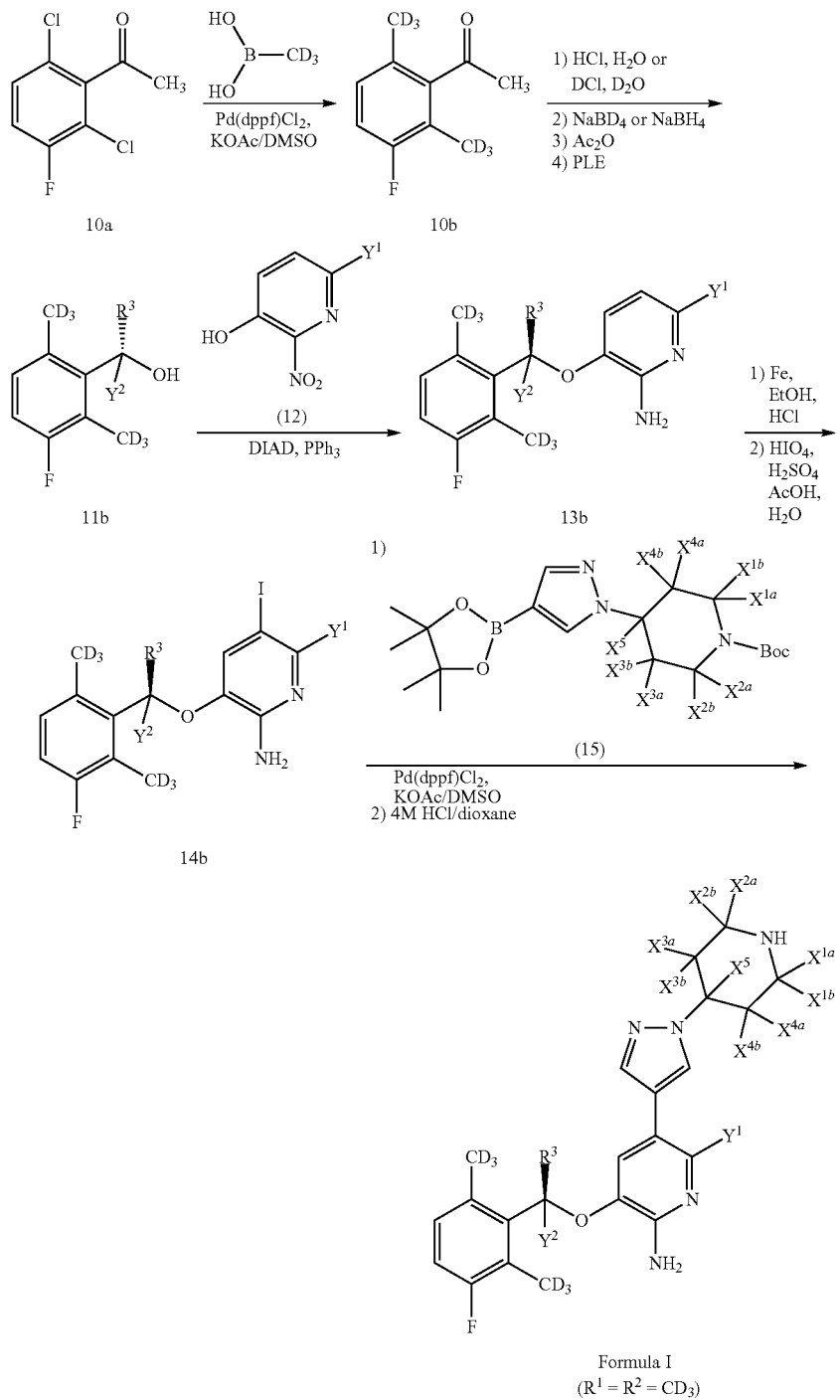

Formula I
($R^1 = R^2 = CD_3$)

New chemical entities corresponding to Formula I can be accessed by multiple step organic synthesis routinely practiced by those skilled in the art and as depicted in Schemes Ia and Ib, above. Commercially available 2',6'-dichloro-3'-fluoroacetophenone 10a may first be subjected to hydrogen-deuterium exchange in the presence of deuterium chloride in deuterium oxide to provide entities where $R^3=CD_3$.

Alternatively 10a may be subjected to Suzuki-Miyaura cross coupling with trideuteromethylboronic acid (commercially available) to provide ketones 10b where $R^1=R^2=CD_3$. Following carbonyl reduction of ketones 10a or 10b with borohydride or borodeuteride the resultant racemic benzylic alcohol is acylated with acetic anhydride. Enzymatic resolution of the mixture of enantiomers may be achieved with pig liver esterase (PLE) to provide chiral alcohols 11a or 11b in greater than 97.5% enantiomeric excess (ee).

Mitsunobu inversion of the secondary alcohol with 2-nitropyridin-3-ols (12 where $Y^1$=H or D) may be achieved with diisopropyl azidodicarboxylate (DIAD) and triphenylphosphine to provide biarylethers 13a or 13b. Following two functional group inter-conversions involving reduction of the nitro group and introduction of iodine at the five position on the pyridine, the scaffold is ready for union with heterocycle 15.

Appropriately deuterated boron-pinacolates, 15, may be united with aryl iodides 13a or 13b via palladium catalyzed cross coupling under alkaline biphasic conditions. Removal of the tert-butylcarbamate (BOC) protecting group with concentrated hydrochloric acid yields the desired active pharmaceutical ingredient as the free base. Preparation of appropriate pharmaceutical grade salt(s) will be necessary and may be accomplished using standard practices.

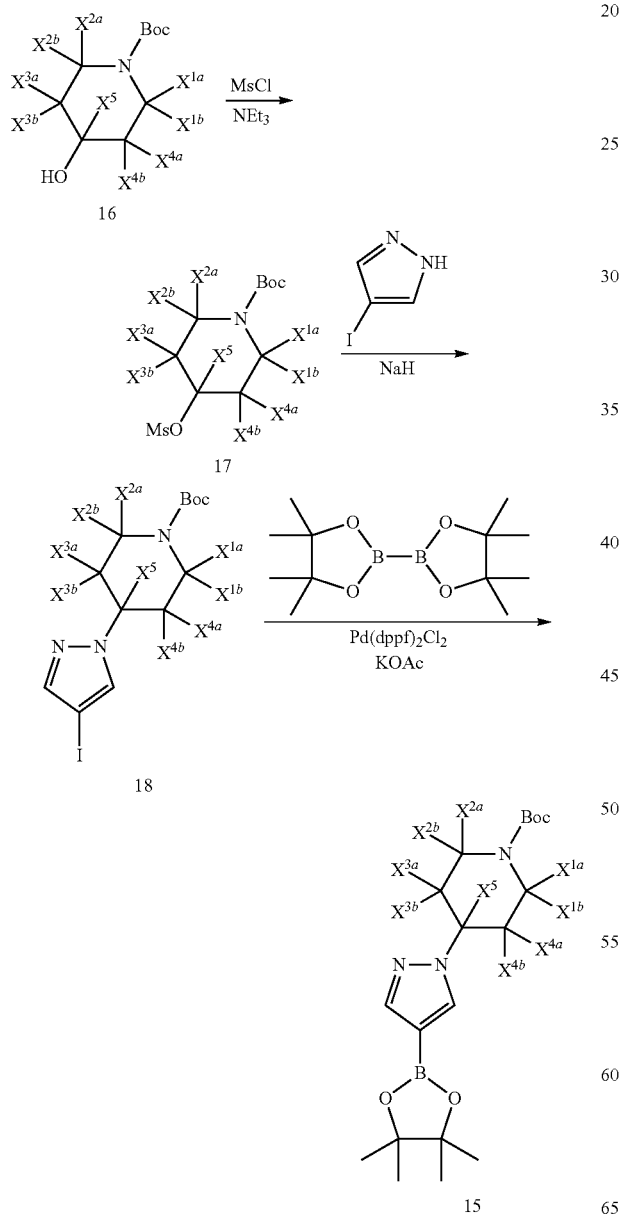

The preparation of functionalized piperidines such as 16a, 16b, and the precursor to 16c and 16d, containing high levels of isotope abundance, has been previously disclosed in patent publication WO 2010/108103. Intermediates 16c and 16d may be prepared from the ketone precursor through reduction with $NaBD_4$ or $NaBH_4$ respectively.

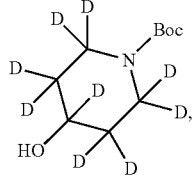

16a

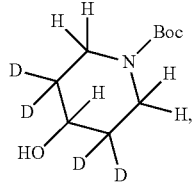

16b

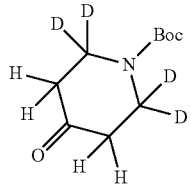

Precursor to 16c and 16d

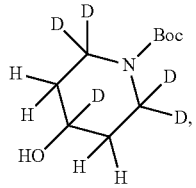

16c

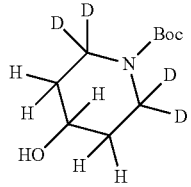

16d

Conversion of the secondary alcohol to the corresponding mesylate allows for installation of the 3-iodo-1-H-pyrazole moiety by direct displacement under anionic conditions. Elaboration of the iodo moiety of 18 to the boron pinacolate, to give 15, is achieved by reaction of dioxoboralane under palladium catalysis.

Suitably deuterated examples of 16 or 17 (Scheme 2) may also be prepared as disclosed in Schemes 2b-2d below:

Scheme 2b: preparation of 16b and 17b:

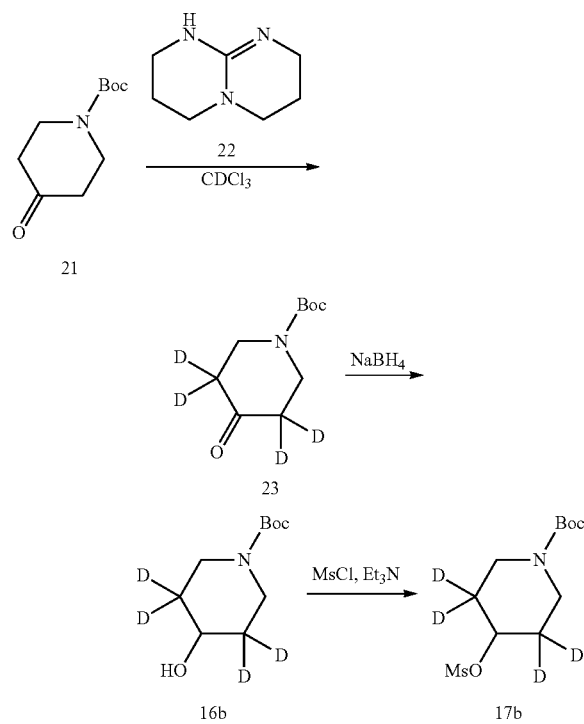

As shown in Scheme 2b, 21 is treated with a base such as 22 and CDCl₃ to give 23. Reduction of the C=O group with NaBH₄ provides 16b. 16b is converted to 17b with mesyl chloride. Analogously, 16f and 17f (shown below) may be prepared by using NaBD₄ instead of NaBH₄ in the C=O reduction step:

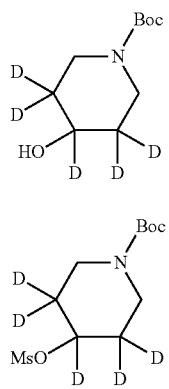

16f

17f

Scheme 2c: preparation of 16d and 17d:

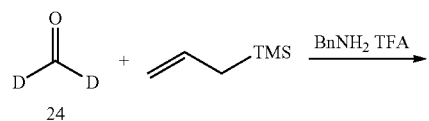

24

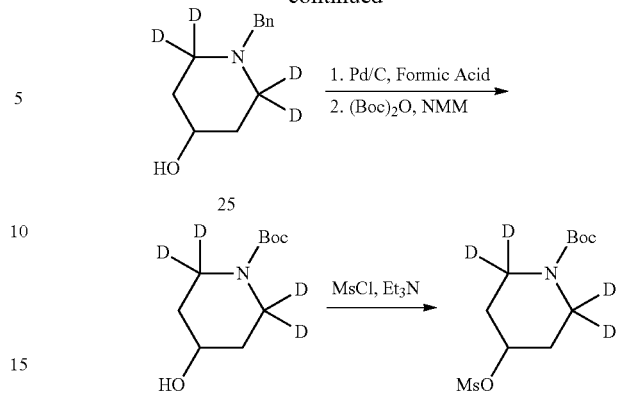

As shown in Scheme 2c, 24 is treated with allyltrimethylsilane and benzylamine to give 25 as described in JLCR, 2007, 50, 131-137 Treatment of 25 with Pd/C and formic acid followed by protection with (Boc)₂O as described in the same as JLCR article affords 16d which gives 17d upon treatment with mesyl chloride.

Scheme 2d: preparation of 16g and 17g:

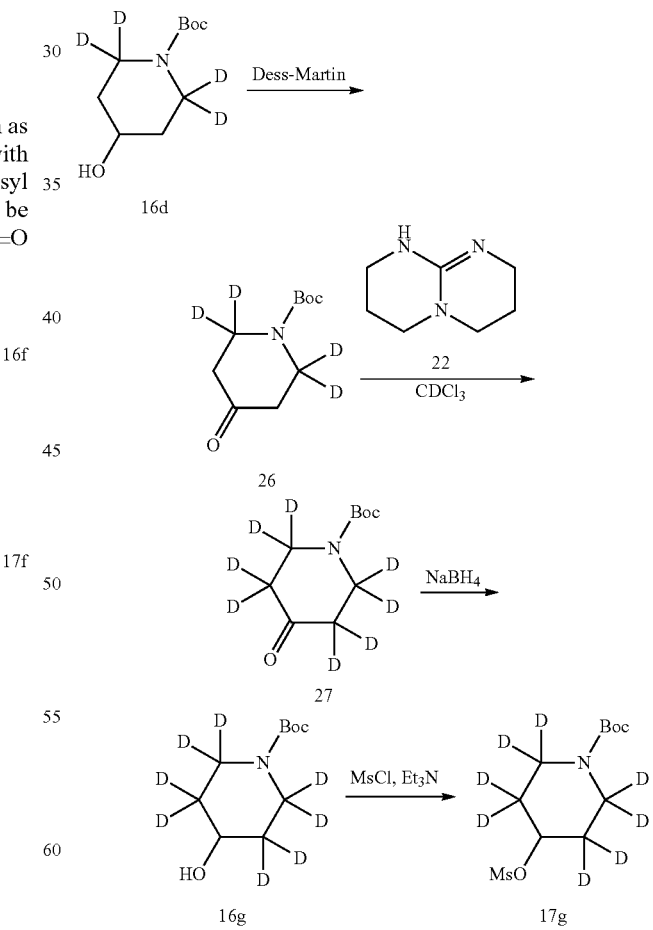

As shown in Scheme 2d, Dess-Martin oxidation of 16d (see Scheme 2c) provides 26, which is treated with 22 and CDCl₃ to give 27. Reduction of the C=O group with NaBH$_4$ gives 16 g, which which gives 17 g upon treatment with mesyl chloride. Analogously, 16 h and 17 h (shown below) may be prepared by using NaBD$_4$ instead of NaBH$_4$ in the C=O reduction step:

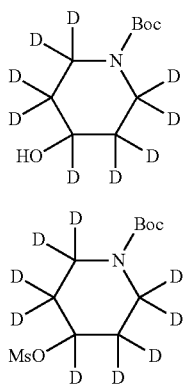

Scheme 3a: Synthetic Route to Intermediate 12b.

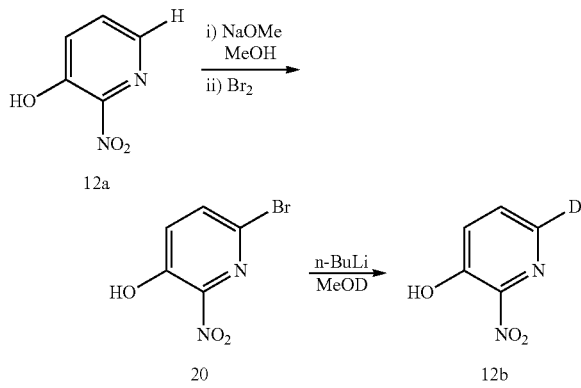

Scheme 3b: Alternate Synthetic Route to Intermediate 12b.

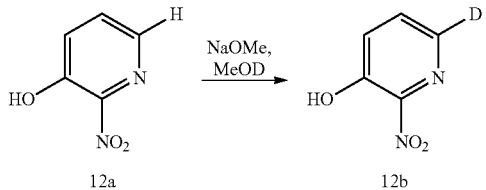

Isotopologues of 2-nitropyridin-3-ol such as 12b where Y$^1$=D may be prepared by regioselective bromination on 2-nitropyridin-3-ol 12a as reported by O'Donnell (J. Med. Chem. 2010, 53, 1222-1237). Halogen metal exchange followed by low temperature quench with appropriate isotope containing electrophile then inserts the desired isotope in correct position. Alternatively, direct hydrogen to deuterium exchange under alkaline conditions and deuterium oxide would yield 12b directly from 12a.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., R$^1$, R$^2$, R$^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula I (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

In some embodiments, the present invention provides a pyrogen-free pharmaceutical composition comprising an effective amount of a compound of Formula I (e.g., including any of the formulae herein), or a pharmaceutical salt of the compound or tautomer; and a pharmaceutically acceptable carrier.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent or a combination of second therapeutic agents. The second therapeutic agent(s) may be selected from any compound or therapeutic agent known to have or that demonstrates advantageous properties when administered with a compound having the same mechanism of action as crizotinib. Such agents include those indicated as being useful in combination with crizotinib, including but not limited to, those described in US 2011003805, and CN101836991.

Preferably, the second therapeutic agent(s) is an agent useful in the treatment or prevention of a cancer, more specifically of prostate cancer, osteosarcomas, lung cancer, particularly non-small cell lung cancer, breast cancer, endometrial cancer, glioblastoma, colorectal cancer, ovarian cancer, pancreatic cancer, kidney cancer, small intestinal cancer, esophageal cancer or gastric cancer.

In one embodiment, the second therapeutic agent is selected from kinase inhibitors. In one aspect of this embodiment, the kinase inhibitor is selected from erlotinib, sorafenib, a deuterated form of erlotinib as disclosed in U.S. patent application Ser. No. 11/957,442 and in U.S. patent application Ser. No. 12/413,510, a deuterated form of sorafenib as disclosed in PCT Patent Application No. PCT/US2009/053595), PF-00299804 and N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutaneamide (See US Patent Publication 2011/0003805). In a more specific embodiment, the deuterated form of erlotinib is compound A,

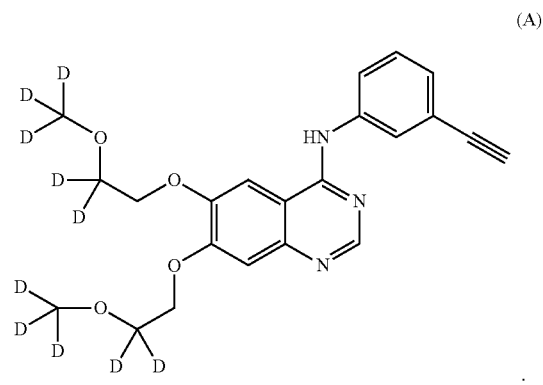 [SMILES: [2H]C([2H])([2H])OC([2H])([2H])COc1cc2ncnc(Nc3cccc(C#C)c3)c2cc1OCC([2H])([2H])OC([2H])([2H])[2H]]

(A)

In another more specific embodiment, the deuterated form of erlotinib is compound B,

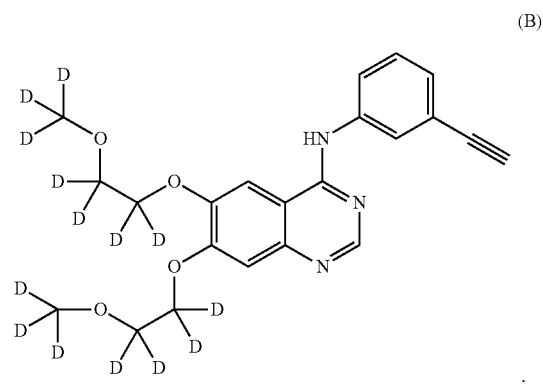 [SMILES: [2H]C([2H])([2H])OC([2H])([2H])C([2H])([2H])Oc1cc2ncnc(Nc3cccc(C#C)c3)c2cc1OC([2H])([2H])C([2H])([2H])OC([2H])([2H])[2H]]

(B)

In one more specific embodiment, the deuterated form of sorafenib is compound C,

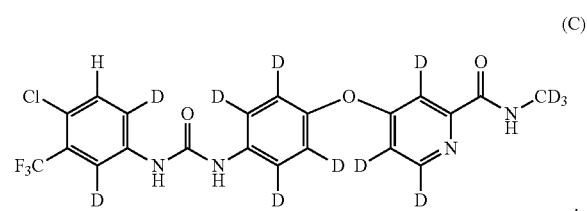 [SMILES: [2H]c1cc(Cl)c(C(F)(F)F)c([2H])c1NC(=O)Nc1c([2H])c([2H])c(Oc2c([2H])c([2H])nc(C(=O)NC([2H])([2H])[2H])c2[2H])c([2H])c1[2H]]

(C)

In one aspect the kinase inhibitor is erlotinib or sorafenib. In one aspect the kinase inhibitor is a deuterated form of erlotinib (as disclosed in the above-referenced patent applications) or a deuterated form of sorafenib (as disclosed in the above-referenced patent application).

In one embodiment, a composition of this invention comprises a combination of the compound of Formula I with two second therapeutic agents selected from kinase inhibitors. In one aspect of this embodiment the combination is with erlotinib or a deuterated form of erlotinib as disclosed in U.S. patent application Ser. No. 11/957,442 and in U.S. patent application Ser. No. 12/413,510, and sorafenib or a deuterated form of sorafenib as disclosed in PCT Patent Application No. PCT/US2009/053595). In a more specific aspect of this embodiment the combination is with erlotinib or compound A, and sorafenib or compound C. In another more specific aspect of this embodiment the combination is with erlotinib or compound B, and sorafenib or compound C. In one aspect of this embodiment the combination is erlotinib and sorafenib. In one aspect of this embodiment the combination is a deuterated form of erlotinib and a deuterated form of sorafenib. In one aspect of this embodiment the combination is a deuterated form of erlotinib and sorafenib. In one aspect of this embodiment the combination is erlotinib and a deuterated form of sorafenib.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from 25 mg to 500 mg per treatment. Treatment is typically administered one to two times daily. In more specific embodiments the effective amount can be one of the following amounts or ranges:

300 mg, preferably administered orally twice a day;
250 mg, preferably administered orally twice a day;
200 mg, preferably administered orally twice a day, or once a day;
100 mg, preferably administered orally once a day;
50 mg, preferably administered orally once a day;
from 200 to 300 mg, preferably administered orally twice a day; or
50-200 mg preferably administered orally once a day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for crizotinib.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of anaplastic lymphoma kinase (ALK) and hepatocyte growth factor receptor (c-met/HGFR) kinase in a cell, comprising contacting a cell with one or more compounds of Formula I herein, or a pharmaceutically acceptable salt thereof.

According to another embodiment, the invention provides a method of treating a disease that is beneficially treated by inhibiting ALK and c-met/HGFR, e.g., crizotinib, in a subject in need thereof, comprising the step of administering to the subject an effective amount of a compound or a composition of this invention. In one embodiment the subject is a patient in need of such treatment. Such diseases are well known in the art and are disclosed in, but not limited to published application WO 2006/021884. Such diseases include, but are not limited to, cancer, in particular, lung cancer, non-small cell lung cancer, bone cancer, pancreatic cancer, skin cancer, head and neck cancer, cutaneous or intraocular melanoma, uterine cancer, ovarian cancer, rectal cancer, cancer of the anal region, stomach cancer, colorectal cancer, colon cancer, gastric cancer, breast cancer, endometrial cancer, carcinoma of the fallopian tubes, carcinoma of the cervix, carcinoma of the vagina, carcinoma of the vulva, Hodgkin's Disease, esophageal cancer, small intestinal cancer, cancer of the endocrine system, cancer of the thyroid gland, cancer of the parathyroid gland, cancer of the adrenal gland, cancer of the urethra, cancer of the penis, cancer of the prostate, chronic or acute leukemia, lymphoma, sarcoma of soft tissue, cancer of the bladder, cancer of the kidney or ureter, renal cell carcinoma, carcinoma of the renal pelvis, neoplasms of the central nervous system (CNS), primary CNS lymphoma, spinal axis tumors, glioblastoma, brain stem glioma, neuroblastoma, pituitary adenoma, solid tumors or a combination of one or more of the foregoing cancers. Such diseases include also abnormal cell growth disorders in which the disease is a benign proliferative disease, including, but not limited to psoriasis, benign prostatic hyperplasia and restinosis.

According to another embodiment, the invention provides a method of treating abnormal cell growth in a mammal.

In one particular embodiment, the method of this invention is used to treat a disease or condition selected from lymphoma, neuroblastoma, solid tumors and non-small cell lung cancer in a subject in need thereof.

Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject in need thereof one or more second therapeutic agents. The choice of second therapeutic agent may be made from any second therapeutic agent known to be useful for co-administration with crizotinib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I, or a pharmaceutically acceptable salt thereof, and a second therapeutic agent to a subject in need thereof for treatment of the following conditions (with the particular second therapeutic agent indicated in parentheses following the indication: non-small cell lung cancer (PF-00299804).

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I, or a pharmaceutically acceptable salt thereof, for use in the treatment or prevention in a subject of a disease, disorder or symptom thereof delineated herein.

EXAMPLES

Example 1

Compound 212

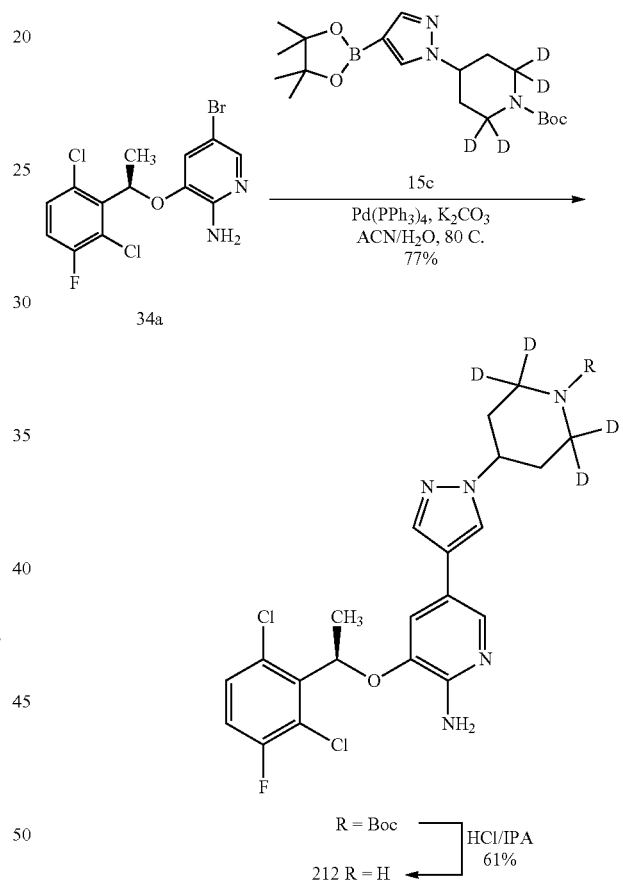

Biarylbromide 34a (69 mg, 0.182 mmol) was dissolved in water (0.455 mL) and acetonitrile (1.3 mL) was added 15c (83.0 mg, 0.218 mmol), $K_2CO_3$ (63.0 mg, 0.165 mmol) and tetrakis(triphenylphoshine)palladium(0) (63 mg, 0.055 mmol). The resulting solution was stirred at 80° C. for 15 hours upon which time LCMS showed complete conversion to desired product. The reaction was concentrated under reduced pressure and directly subjected to silica gel chromatography on an ISCO Combiflash purification system, 0-10% methanol/dichloromethane gradient. The fractions containing the desired product were combined and concentrated to give a colorless oil (75 mg, 0.141 mmol, 77%).

The resulting oil was dissolved in a solution of hydrochloric acid in isopropanol (4M, 0.1 mL) and stirred for 2 h upon which time LCMS showed complete conversion to desired product. The reaction was diluted with ethyl acetate and water. The phases were separated and aqueous phase was extracted with ethyl acetate. The combined organic phases were washed with aqueous hydrochloric acid (1M). The combined aqueous layers were then basified with aqueous sodium hydroxide (3N). The desired product was then extracted with ethyl acetate (3×). The organic phases were dried over sodium sulfate, filtered and concentrated to give a colorless oil which was dissolved in binary benzene/methanol solvent pair. The solution was cooled to −78 C with a dry ice/acetone bath and the resulting solid was subjected to lyophilization which yielded compound 212 as a white powder (39 mg, 0.086 mmol, 61% yield).

(R)-3-(1-(2,6-dichloro-3-fluorophenyl)ethoxy)-5-(1-(2,2,6,6-tetradeuteropiperidin-4-yl)-1H-pyrazol-4-yl)pyridin-2-amine 212. $^1$H NMR (400 MHz, CDCl$_3$) δ: 7.74 (br s, 1H), 7.56 (d, J=4 Hz, 1H), 7.49 (s, 1H), 7.31 (dd, J=8, 4 Hz, 1H), 7.04 (m, 1H), 6.86 (br s, 1H), 6.07 (q, 1H), 4.79 (br s, 2H), 4.21 (m, 1H), 2.15 (m, 2H), 1.90 (m, 2H), 1.86 (d, J=12 Hz, 3H), MS (ESI) 454.2 [(M+H)$^+$].

Example 2

Compound 211

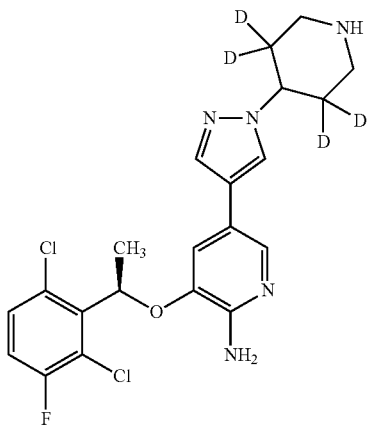

Compound 211 was prepared using a procedure similar to the one disclosed in Example 1 above.

(R)-3-(1-(2,6-dichloro-3-fluorophenyl)ethoxy)-5-(1-(3,3,5,5-tetradeuteropiperidin-4-yl)-1H-pyrazol-4-yl)pyridin-2-amine 211 obtained as white powder (41 mg, 0.087 mmol) ($^1$H NMR (400 MHz, CDCl$_3$) δ: 7.74 (br s, 1H), 7.56 (d, J=4 Hz, 1H), 7.49 (s, 1H), 7.31 (dd, J=8, 4 Hz, 1H), 7.04 (m, 1H), 6.86 (br s, 1H), 6.07 (q, 1H), 4.79 (br s, 2H), 4.21 (m, 1H), 3.21 (d, J=12 Hz, 2H), 2.73 (d, J=12 Hz, 2H), 1.86 (d, J=6.7 Hz, 3H), MS (ESI) 454.2 [(M+H)$^+$].

Example 3

Compound 215

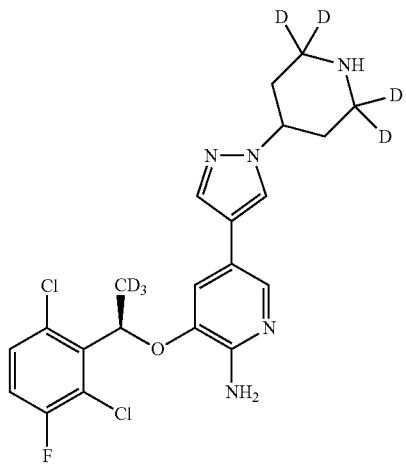 [SMILES: [2H]C1([2H])CC(n2cc(-c3cnc(N)c(O[C@@H](c4c(Cl)ccc(F)c4Cl)C([2H])([2H])[2H])c3)cn2)CC([2H])([2H])N1]

Compound 215 was prepared using a procedure similar to the one disclosed in Example 1 above.

(R)-5-(1-(2,2,6,6-tetradeuteropiperidin-4-yl)-1H-pyrazol-4-yl)-3-(2,2,2-trideutero-1-(2,6-dichloro-3-fluorophenyl)ethoxy)pyridin-2-amine 215 obtained as an off white powder (11 mg, 0.024 mmol) $^1$H NMR (400 MHz, CDCl$_3$) δ: 7.74 (br s, 1H), 7.56 (d, J=4 Hz, 1H), 7.49 (s, 1H), 7.31 (dd, J=8, 4 Hz, 1H), 7.04 (m, 1H), 6.86 (br s, 1H), 6.07 (s, 1H), 4.79 (br s, 2H), 4.21 (m, 1H), 2.15 (m, 2H), 1.90 (m, 2H), MS (ESI) 458.4 [(M+H)$^+$]

Example 4

Compound 214

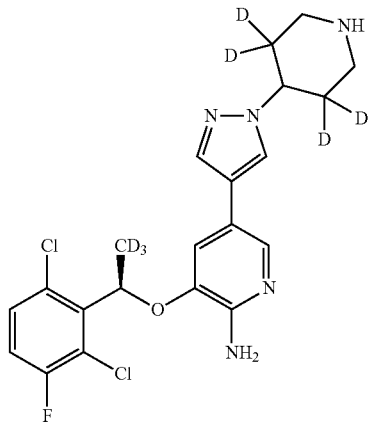 [SMILES: [2H]C1([2H])CNCC([2H])([2H])C1n1cc(-c2cnc(N)c(O[C@@H](c3c(Cl)ccc(F)c3Cl)C([2H])([2H])[2H])c2)cn1]

Compound 214 was prepared using a procedure similar to the one disclosed in Example 1 above. Without further purification of the reaction product, an $^1$H NMR was taken (disclosed below) that suggests that 214 is the major component of the mixture.

(R)-5-(1-(3,3,5,5-tetradeuteropiperidin-4-yl)-1H-pyrazol-4-yl)-3-(2,2,2-trideutero-1-(2,6-dichloro-3-fluorophenyl)ethoxy)pyridin-2-amine 214 ($^1$H NMR (400 MHz, CDCl$_3$) δ: 7.74 (br s, 1H), 7.56 (d, J=4 Hz, 1H), 7.49 (s, 1H), 7.31 (dd, J=8, 4 Hz, 1H), 7.04 (m, 1H), 6.86 (br s, 1H), 6.07 (q, 1H), 4.79 (br s, 2H), 4.21 (m, 1H), 3.21 (d, J=12 Hz, 2H), 2.73 (d, J=12 Hz, 2H). MS (ESI) 458.4 [(M+H)⁺]. Exemplary biarylbromides (such as 34a employed in Example 1) that may be used in the preparation of compounds herein are disclosed below:

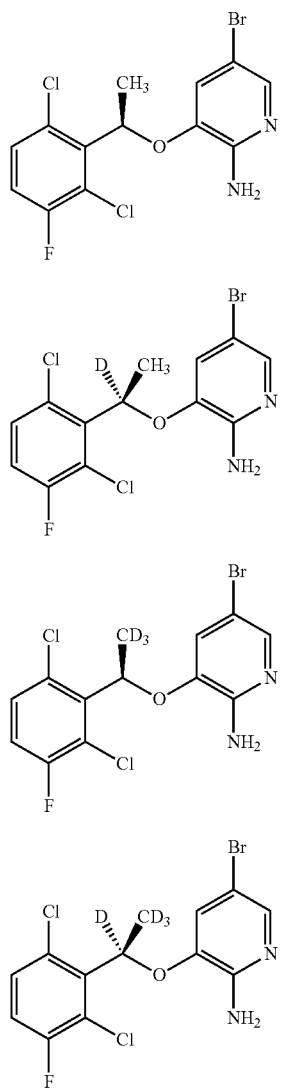

Synthesis of biarylbromides 34a-d

Example 5

Preparation of 34d

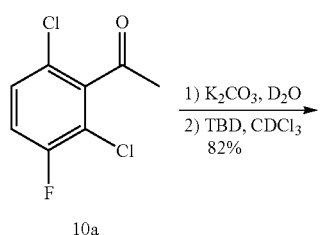

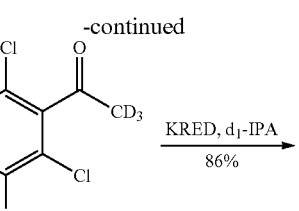

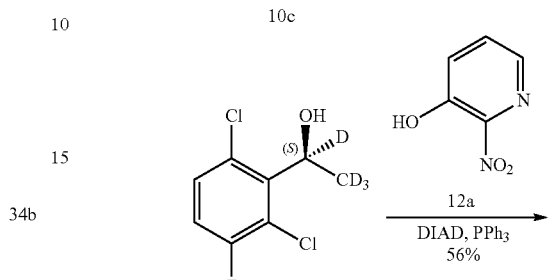

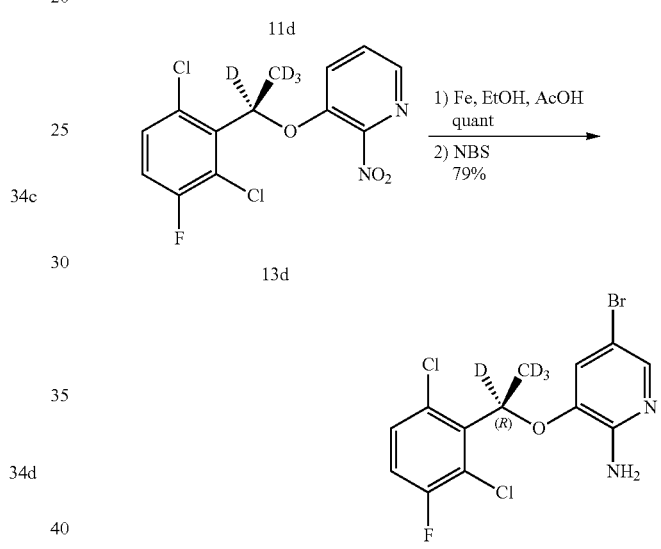

Preparation of Intermediate 10c

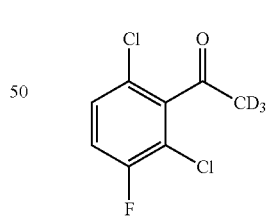

Commercially available 1-(2,6-dichloro-3-fluorophenyl)ethanone 10a (3.4 g, 16.4 mmol) was subjected to H-D exchange with potassium carbonate (250 mg) in D₂O (10 mL) at reflux. The deuterium enrichment was assayed by ¹H NMR to be 85%. The reaction was neutralized with aqoues HCl and the product extracted with ethyl acetate. The combined organics were dried over sodium sulfate, filtered and concentrated. The material was subjected to further H-D exchange catalyzed by 1,5,7-triazabicyclo[4.4.0]dec-5-ene (0.2 g) in CDCl₃ (16 mL). The solution was stirred at ambient temperature and pressure overnight. After 12 h ¹H NMR indicated deuterium enrichment was sufficient (>99%). The reaction was diluted with dichloromethane and washed with aqueous hydrochloric acid (1M) and brine. The organic layer was dried over sodium sulfate, filtered and concentrated to give 2,2,2-trideutero-1-(2,6-dichloro-3-fluorophenyl)ethanone (10c) as a colorless oil (2.84 g, 82% yield). This material was carried into the enzymatic reaction without any further purification.

Preparation of Intermediate 11d

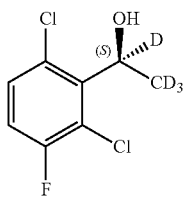

11d 2,2,2-Trideutero-1-(2,6-dichloro-3-fluorophenyl)ethanone (10a, 1.29 g) was dissolved in 30% aqueous triethanolamine solution (pH 7) and $d_1$-ispropanol (5 g). Ketoreductase enzyme (KRED-P1-H08, 50 mg) and NADP$^+$ (50 mg) were added as single portions. The reaction was stirred under a positive stream of nitrogen as deemed by outlet needle attachment to oil bubbler. Conversion to desired was quantified by LCMS and after 3d additional enzyme (50 mg), NADP$^+$ (50 mg) and $d_1$-ispropanol (5 g) were added. The reaction was allowed to proceed for 4d additional upon which time LCMS showed complete conversion to desired product. The reaction was diluted with heptanes (20 mL) and heated to 40° C. for 1 h. The resulting suspension was diluted with ethyl acetate and water and filtered through a short pad of celite. The resulting biphasic mixture was separated and aqueous was back extracted with ethyl acetate. The combined organic phases were washed sequentially with aqueous sodium bicarbonate, ammonium chloride, and brine. The organic layer was dried over sodium sulfate, filtered and concentrated to give 1-deutero-1-(2,6-dichloro-3-fluorophenyl)-2,2,2-trideuteroethanol 11d as a colorless oil (1.1 g, 86% yield, >99% isotopic enrichment). This material was carried into the enzymatic reaction without any further purification.

Preparation of Intermediate 13d

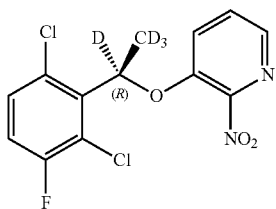

13d

A tetrahydrofuran solution (43 mL) of 1-deutero-1-(2,6-dichloro-3-fluorophenyl)-2,2,2-trideuteroethanol (1.00 g, 4.76 mmol), 3-hydroxy aminopyridine (733 mg, 5.23 mmol), and triphenylphosphine (1.87 g, 7.14 mmol) was prepared at ambient temperature and then cooled to OC with ice bath. Diisopropyl azodicarboxylate (1.0 mL) was added by syringe. The reaction was allowed to warm to ambient temperature over 12 h at which point LCMS confirmed conversion of chiral alcohol to biaryl ether. The reaction was concentrated under reduced pressure and directly subjected to silica gel chromatography on an ISCO Combiflash purification system, 0-30% ethylacetate/heptanes gradient. The fractions containing the desired biaryl ether were combined and concentrated to give (R)-3-(1-(2,6-dichloro-3-fluorophenyl)-1,2,2,2-tetradeuterooethoxy)nitropyridine (13d) as a white solid (0.89 g, 56%).

Preparation of Intermediate 34d

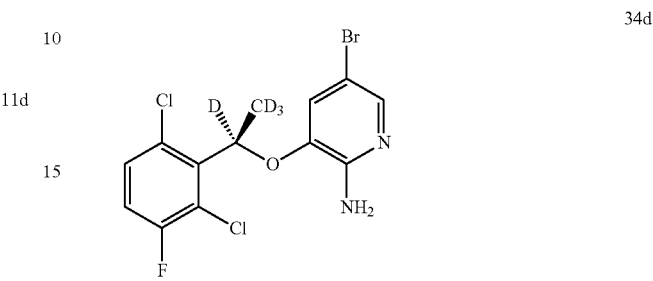

34d (R)-3-(1-(2,6-dichloro-3-fluorophenyl)-1,2,2,2-tetradeuteroethoxy)nitropyridine (13d) (0.889 mg, 2.66 mmol) was dissolved in solution of ethanol and acetic acid (133 mL 1:1.15). Iron powder (1.49 g) was added a solid portion. The suspension was heated to a gentle reflux for 1 h at which LCMS deemed complete conversion to amino pyridine. The reaction was cooled, diluted with diethyl ether and carefully neutralized with aqueous potassium carbonate in ice. The biphasic solution was then brought to basic pH was sodium hydroxide at which point the product was extracted with diethyl ether. The combined organic phases were dried over sodium sulfate, filtered and concentrated to give (R)-3-(1-(2,6-dichloro-3-fluorophenyl)-1,2,2,2-tetradeuterooethoxy)pyridine-2-amine as an off white solid (1.0 g). The material was carried forward without further purification.

(R)-3-(1-(2,6-dichloro-3-fluorophenyl)-1,2,2,2-tetradeuterooethoxy)pyridine-2-amine (2.66 mmol) was dissolved in dichloromethane (10 mL) and cooled to OC with an ice bath. An acetonitrile solution (1 mL) of N-bromosuccinimide (2.66 mmol) was added by syringe. After 1 h LCMS indicated complete conversion to desired bromide. The reaction was concentrated under reduced pressure and directly subjected to silica gel chromatography on an ISCO Combiflash purification system, 0-100% ethylacetate/heptanes gradient. The fractions containing the desired bromide were combined and concentrated to give (R)-5-bromo-3-(1-deutero-1-(2,6-dichloro-3-fluorophenyl)-2,2,2-trideuterooethoxy)pyridin-2-amine (34d) as a tan solid (820 mg, 2.12 mmol).

Example 6

Preparation of 34a

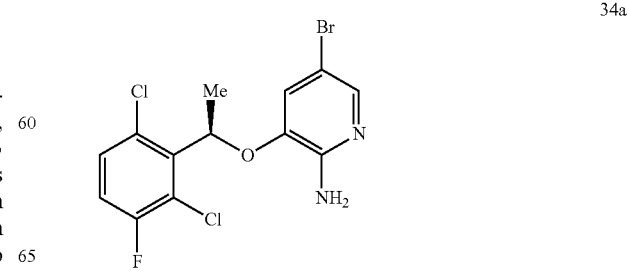

34a (R)-5-bromo-3-(1-(2,6-dichloro-3-fluorophenyl)ethoxy)pyridin-2-amine (34a) was prepared according to the procedures described by de Koning, P. D. et al. *Org. Res. Process Dev.* 2011, 15, 1018-1026.

Example 7

Preparation of 34b

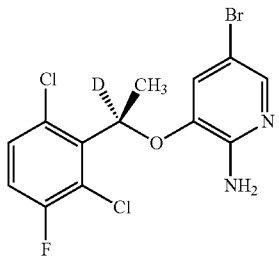

34b (R)-5-bromo-3-(1-deutero-1-(2,6-dichloro-3-fluorophenyl)-ethoxy)pyridin-2-amine (34b) may be prepared using a procedure similar to the one disclosed for the synthesis of biarylbromide 34d (Example 5). Accordingly, Example 5 is modified by subjecting commercially available 1-(2,6-dichloro-3-fluorophenyl)ethanone 10a to enzymatic reduction without prior H-D exchange of the methyl group hydrogens of 10a.

Example 8

Preparation of 34c

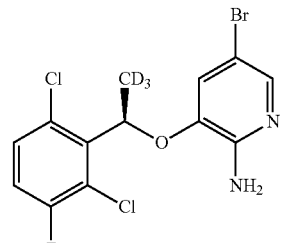

34c (R)-5-bromo-3-(1-(2,6-dichloro-3-fluorophenyl)-2,2,2-trideuteroethoxy)pyridin-2-amine (34c) was prepared using a procedure similar to the one disclosed for biarylbromide 34d (Example 5). Accordingly, Example 5 was modified by replacing $d_1$-isopropanol with isopropanol in the reduction of 10c to ultimately provide 34c in good yield as a single stereoisomer.

Example 9

Preparation of 16b-16h

Exemplary deuterated 4-Boc-piperdin-1-ols 16b-16h useful for the preparation of piperidine-pyrazole boroxalanes such as 15b-h may be prepared as shown in Scheme 4 below.

Scheme 4: Preparation of compounds 16b-16h:

(1)

(2)

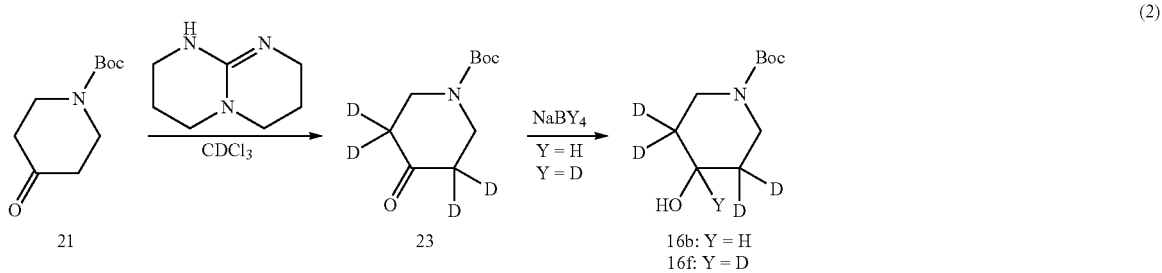

(3)

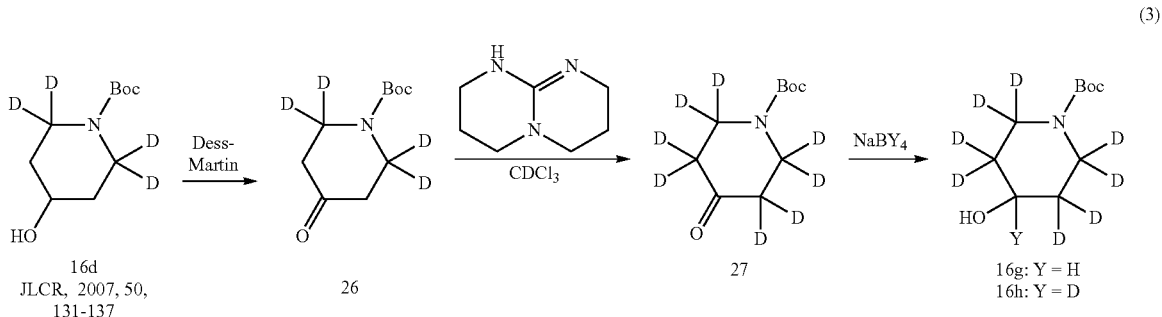

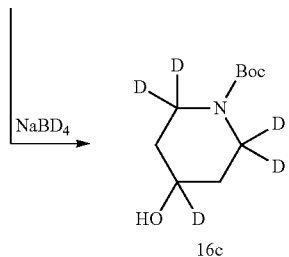

(4)

16c

Preparation of 23.

tert-butyl 3,3,5,5-tetradeutero-4-oxopiperidine-1-carboxylate (23): 1-Boc-4-piperidone (10 g, 50.2 mmol) was dissolved in CDCl$_3$ (100 mL). 1,5,7-Triazabicyclo[4.4.0]dec-5-ene (0.5 g) was added as a single portion and the solution was stirred at ambient temperature and pressure overnight. The deuterium enrichment was assayed by $^1$H NMR and the reaction was deemed complete when resonances assigned to the protons alpha to the carbonyl were no longer visible by $^1$H NMR. The reaction was neutralized with aqueous hydrochloric acid (1M) and the product extracted with ethyl acetate. The combined organics were dried over sodium sulfate, filtered and concentrated to give tert-butyl 3,3,5,5-tetradeutero-4-oxopiperidine-1-carboxylate 23 as a colorless oil (8.72 g, 43.0 mmol, 86% yield, >99% D4) $^1$H NMR (400 MHz, CDCl$_3$) δ: 3.71 (s, 4H), 1.47 (s, 9H).

Preparation of 16b.

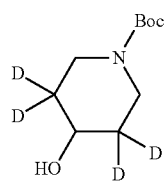

16b tert-butyl 3,3,5,5-tetradeutero-4-hydroxypiperidine-1-carboxylate 16b: tert-butyl 3,3,5,5-tetradeutero-4-oxopiperidine-1-carboxylate 23 (1.1 g, 5.41 mmol) was dissolved in methanol (10 mL) and cooled to 0° C. with an ice bath. Sodium borohydride (0.2 g) was added as a single portion and the solution was stirred at ambient temperature and pressure for 12 h. The reaction was neutralized with aqueous saturated ammonium chloride, volatiles concentrated, and then re-partitioned with water and ethyl acetate. The product was extracted with ethyl acetate. The combined organics were dried over sodium sulfate, filtered and concentrated to give tert-butyl 3,3,5,5-tetradeutero-4-hydroxypiperidine-1-carboxylate 16b as a colorless oil (0.955 g, 4.65 mmol, 86% yield, >99% D4) $^1$H NMR (400 MHz, CDCl$_3$) δ: 3.84-3.81 (br s, 3H), 2.99 (d, J=4 Hz, 2H), 1.47 (s, 9H); MS (ESI) 206.2 [(M+H)$^+$].

Preparation of 16f.

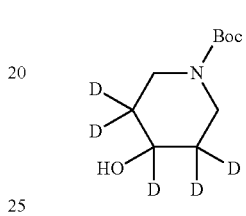

16f tert-butyl 3,3,4,5,5-pentadeutero-4-hydroxypiperidine-1-carboxylate 16f: tert-butyl 3,3,5,5-tetradeutero-4-oxopiperidine-1-carboxylate 23 (2.0 g, 9.84 mmol) was dissolved in methanol (16 mL) and cooled to 0° C. with an ice bath. Sodium borohydride (0.4 g) was added as a single portion and the solution was stirred at ambient temperature and pressure for 12 h. The reaction was neutralized with aqueous saturated ammonium chloride, volatiles concentrated, and then re-partitioned with water and ethyl acetate. The product was extracted with ethyl acetate. The combined organics were dried over sodium sulfate, filtered and concentrated to give tert-butyl 3,3,4,5,5-pentadeutero-4-hydroxypiperidine-1-carboxylate 16f as a colorless oil (1.75 g, 8.53 mmol, 87% yield, >99% D$_5$) $^1$H NMR (400 MHz, CDCl$_3$) δ: 3.84 (d, J=16 Hz, 2H), 3.00 (d, J=16 Hz, 2H), 1.47 (s, 9H); MS (ESI) 207.2 [(M+H)$^+$].

Preparation of 16d.

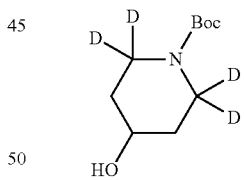

16d tert-butyl 2,2,6,6-tetradeutero-4-hydroxypiperidine-1-carboxylate 16d was prepared as described by Hesk, D. et al. J. Label Compd Radiopharm. 2007; 50: 131-137.

Preparation of 26.

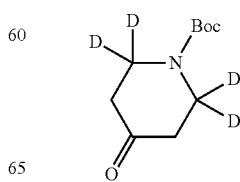

26 tert-butyl 2,2,6,6-tetradeutero-4-oxopiperidine-1-carboxylate 26: A suspension of sodium bicarbonate (4.0 g), 4 Å molecular sieves (4.0 g) and 16d (1.66 g, 8.1 mmol) was prepared in dichloromethane (41 mL). Dess-Martin periodinane (3.82 g, 8.9 mmol) was then added as a solid portion. The reaction was allowed to proceed for 12 h upon which it was deemed complete by TLC. Sodium thiosulfate (4 g) was added and a solvent swap with heptanes was achieved by co-distillation. The resulting slurry was filtered through a short pad of celite which was washed with a 30% ethyl acetate/heptanes solvent pair. The filtrate was then sequentially washed with 10% sodium sulfite, saturated aqueous sodium thiosulfate, sodium bicarbonate and brine. The partitioned organic phase was dried over sodium sulfate, filtered and concentrated to give tert-butyl 2,2,6,6-tetradeutero-4-oxopiperidine-1-carboxylate 26 as a white powder (8.1 mmol, 99% yield, >99% D4) $^1$H NMR (400 MHz, CDCl$_3$) δ: 2.43 (s, 4H), 1.47 (s, 9H). Residual periodinane resonances were undetectable in the $^1$H NMR. The material was deemed sufficiently pure to carry forward.

Preparation of 27.

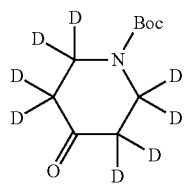

tert-butyl 2,2,3,3,5,5,6,6-octadeutero-4-oxopiperidine-1-carboxylate 27: Deuterium enrichment was achieved by direct H-D exchange with ketone 26 (8.1 mmol) and TBD catalyst (0.2 g) in CDCl$_3$ (40 mL) as described for tert-butyl 3,3,5,5-tetradeutero-4-oxopiperidine-1-carboxylate 23. tert-butyl 2,2,3,3,5,5,6,6-octadeutero-4-oxopiperidine-1-carboxylate 27 was obtained as a colorless oil (1.54 g, 7.44 mmol, 92% yield, >99% D$_8$. $^1$H NMR (400 MHz, CDCl$_3$) δ: 1.47 (s, 9H).

Preparation of 16g.

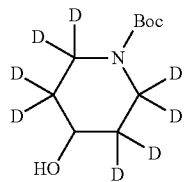

tert-butyl 2,2,3,3,5,5,6,6-octadeutero-4-hydroxypiperidine-1-carboxylate 16g was prepared from the reaction of ketone 27 (0.55 g, 2.68 mmol) with sodium borohydride (0.1 g) in methanol as described for alcohol 16b to give 16g (0.35 g, 1.65 mmol, 62% yield) as a colorless oil. $^1$H NMR (400 MHz, CDCl$_3$) δ: 3.81 (br s, 1H), 1.47 (s, 9H).

Preparation of 16h.

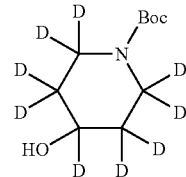

tert-butyl 2,2,4,3,3,5,5,6,6-nonadeutero-4-hydroxypiperidine-1-carboxylate 16h was prepared from the reaction of ketone 27 (0.55 g, 2.68 mmol) with sodium borodeuteride (0.12 g) in methanol as described for alcohol 16f to give 16h (0.39 g, 1.84 mmol, 66% yield) as a colorless oil. $^1$H NMR (400 MHz, CDCl$_3$) δ: 1.47 (s, 9H).

Preparation of 16c.

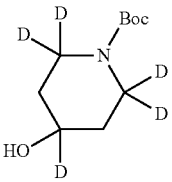

tert-butyl 2,2,4,6,6-pentadeutero-4-hydroxypiperidine-1-carboxylate 16c is prepared from ketone 26 with sodium borodeuteride as described for the preparation of alcohol 16f.

Preparation of 16e.

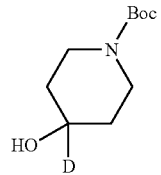

tert-butyl 4-deutero-4-hydroxypiperidine-1-carboxylate 16e is prepared from commercially available ketone 21 with sodium borodeuteride as described for the preparation of alcohol 16f.

Exemplary piperidine-pyrazole boroxalanes that may be used in the preparation of compounds herein are disclosed below:

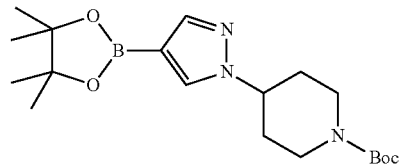

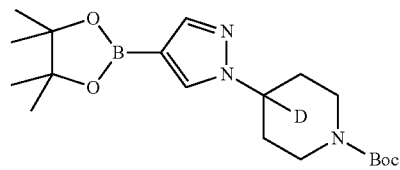

-continued

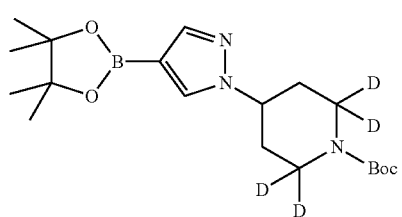
15c

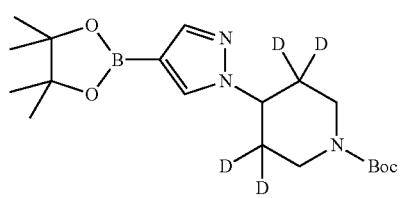
15d

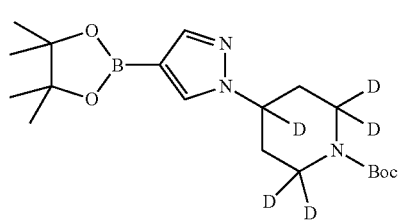
15e

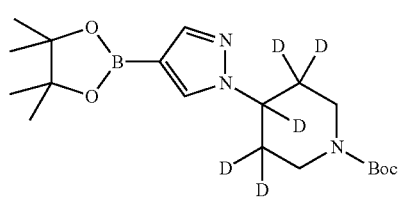
15f

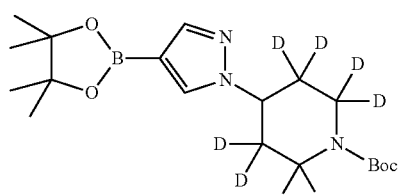
15g

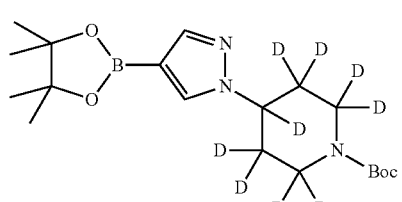
15h

Example 10

Preparation of 15c

Scheme 5: Preparation of 15c:

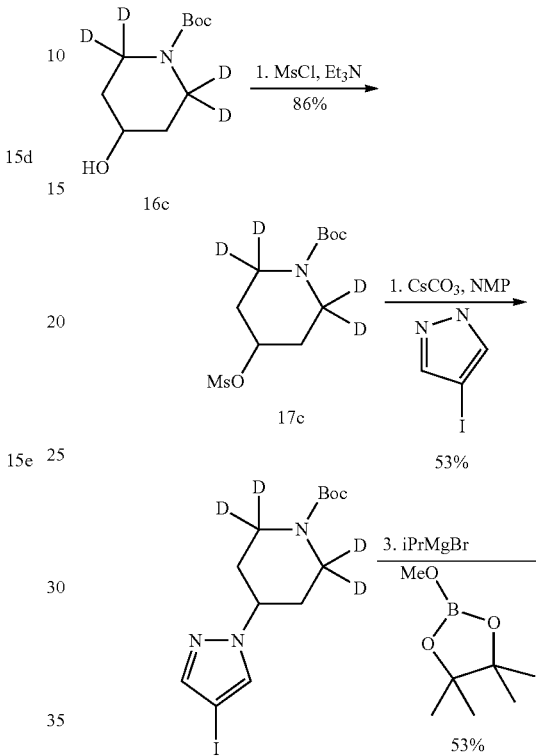

Preparation of Intermediate 17c.

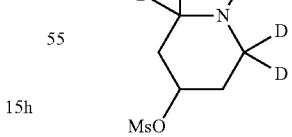
17c tert-butyl 2,2,6,6-tetradeutero-4-((methylsulfonyl)oxy)piperidine-1-carboxylate 17c: Alcohol 16c (0.78 g, 3.81 mmol) and N-methylmorpholine (0.46 mL) were dissolved in dicholoromethane (10 mL) and then cooled to 0C with an ice bath. Methanesulfonyl chloride (0.3 mL) was then added by syringe as a single portion. After 10 minutes the bath was removed and the reaction was warmed to ambient temperature for 2 h at which point the reaction was deemed complete by TLC. The reaction was diluted with dichloromethane and then quenched with aqueous hydrochloride (1M). The phases were separated and the organic phase was then washed with aqueous hydrochloride, brine, and water. The combined organics were dried over sodium sulfate, filtered and concentrated to give an off white solid (3.81 mmol, >95% yield). tert-butyl 2,2,6,6-tetradeutero-4-((methylsulfonyl)oxy)piperidine-1-carboxylate 17c: $^1$H NMR (400 MHz, CDCl$_3$) δ: 4.89 (m, 1H), 3.04 (s, 3H), 1.95 (dd, J=12, 4 Hz, 2H), 1.80 (dd, J=16, 8 Hz, 2H), 1.46 (s, 9H).

Preparation of Intermediate 18c.

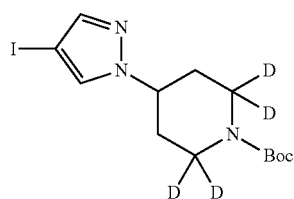

18c tert-butyl 2,2,6,6-tetradeutero-4-(4-iodo-1H-pyrazol-1-yl)piperidine-1-carboxylate 18c: Cesium carbonate (1.63 g) is added to a solution of 4-iodo-pyrazole (0.81 g, 4.17 mmol) in N-methyl pyrrolidinone (NMP, 3.5 mL). The solution is heated to 80 C at which point a NMP solution of mesylate 17c (3.81 mmol) is added as a single portion and the reaction is stirred for 12 h at which point the reaction is deemed complete by LCMS. The reaction was cooled, concentrated under reduced pressure and directly subjected to silica gel chromatography on an ISCO Combiflash purification system, 0-40% acetone/heptanes gradient. The fractions containing the desired product were combined and concentrated to give colorless oil (0.45 g, 1.19 mmol, 32%). tert-butyl 2,2,6,6-tetradeutero-4-(4-iodo-1H-pyrazol-1-yl)piperidine-1-carboxylate 18c: $^1$H NMR (400 MHz, CDCl$_3$) δ: 7.53 (s, 1H), 7.46 (s, 1H), 4.29 (m, 1H), 2.09 (dd, J=12, 4 Hz, 2H), 1.85 (m, 2H), 1.46 (s, 9H).

Preparation of 15c.

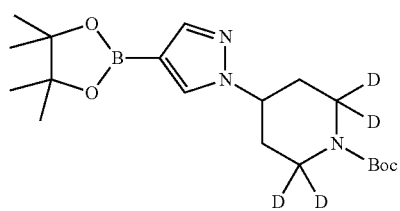

15c tert-butyl, 2,2,6,6-tetradeutero-4-(4-(4,4,5,5-tetramethyl-1,3,2-dioxaborolan-2-yl)-1H-pyrazol-1-yl) piperidine-1-carboxylate 15c: Pyrazole iodide 18c (0.45 g, 1.2 mmol) was dissolved in tetrahydrofuran (5 mL) and then cooled to 0° C. A solution of isopropyl magnesium chloride in 2-methyl-THF (0.74 mL, 2.4M) was then added dropwise. After 15 minutes 2-methoxy-4,4,5,5-tetramethyl-1,3,2-dioxaborolane (0.41 mL) was added by syringe. The reaction was allowed to warm to ambient temperature over 12 h at which time it was deemed complete by LCMS. The reaction was quenched with an aqueous solution of saturated ammonium chloride and volatiles were removed under reduced pressure. The reaction was then partitioned between ethyl acetate and water. The organic phases were washed sequentially with saturated ammonium chloride and brine. The combined organics were dried over sodium sulfate, filtered, concentrated and purified by silica gel chromatography on an ISCO Combiflash purification system, 0-50% ethyl acetate/heptanes gradient. The fractions containing the desired product were combined and concentrated to give colorless oil (0.34 g, 0.89 mmol, 75%). tert-butyl, 2,2,6,6-tetradeutero-4-(4-(4,4,5,5-tetramethyl-1,3,2-dioxaborolan-2-yl)-1H-pyrazol-1-yl)piperidine-1-carboxylate 15c: $^1$H NMR (400 MHz, CDCl$_3$) δ: 7.86 (s, 1H), 7.77 (s, 1H), 4.29 (m, 1H), 2.09 (m, 2H), 2.1 (m, 2H), 1.49 (s, 9H), 1.33 (s, 12H).

Piperidine-pyrazole boroxalanes such as 15a, 15b and 15d-h may be prepared from the corresponding 4-hydroxypiperidines as described for compound 15c in Example 10 above. For example, compound 15a may be prepared as described in Example 10 from commercially available tert-butyl 4-hydroxypiperidine-1-carboxylate (CAS 109384-19-2). Compound 15b may be prepared as described in Example 10 from compound 16e. Compound 15d may be prepared as described in Example 10 from compound 16d. Compound 15e may be prepared as described in Example 10 from compound 16c. Compound 15f may be prepared as described in Example 10 from compound 16f. Compound 15g may be prepared as described in Example 10 from compound 16g. Compound 15h may be prepared as described in Example 10 from compound 16h.

Biological Assays:

Example 11

Evaluation of Metabolic Stability

Microsomal Assay: Human liver microsomes (20 mg/mL) are obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are purchased from Sigma-Aldrich.

Determination of Metabolic Stability: 7.5 mM stock solutions of test compounds are prepared in DMSO. The 7.5 mM stock solutions are diluted to 12.5-50 μM in acetonitrile (ACN). The 20 mg/mL human liver microsomes are diluted to 0.625 mg/mL in 0.1 M potassium phosphate buffer, pH 7.4, containing 3 mM MgCl$_2$. The diluted microsomes are added to wells of a 96-well deep-well polypropylene plate in triplicate. A 10 μL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 μM test compound, and 2 mM NADPH in 0.1 M potassium phosphate buffer, pH 7.4, and 3 mM MgCl$_2$. The reaction mixtures are incubated at 37° C., and 50 μL aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula I and the positive control, 7-ethoxycoumarin (1 μM). Testing is done in triplicate.

Data analysis: The in vitro $t_{1/2}$s for test compounds are calculated from the slopes of the linear regression of % parent remaining (ln) vs incubation time relationship.

in vitro $t_{1/2}$=0.693/k k=−[slope of linear regression of % parent remaining(ln) vs incubation time]

Data analysis is performed using Microsoft Excel Software.

Example 12

Method for Assessment of $IC_{50}$ Shift

Human liver microsomes (0.25 mg/mL) were pre-incubated with 100, 50, 25, 12.5, 6.25, 3.125, 1.563, 0.781, 0.391, 0.195, 0.098, and 0 mM of Crizotinib for 0 and 30 min, in the presence of 2 mM NADPH, in shallow 96-well plates. To measure residual CYP3A4 enzyme activity after pre-incubation, aliquots of the reaction mixtures were diluted 1:10 in 0.1 M potassium phosphate buffer, pH 7.4, containing 3 mM $MgCl_2$, in separate shallow 96-well plates. Testosterone (final concentration 50 mM) was added and the reactions were initiated by addition 2 mM NADPH. These reactions were incubated for another 10 min and then stopped by the addition of acetonitrile with internal standard. The plates were centrifuged to pellet precipitated protein, and supernatants were analyzed by LC-MS/MS for amounts of 6β-OH-testosterone formed.

The same assay was run another two times, each time with a different representative test compound instead of crizotinib: the test compounds in the two runs were, respectively, Compound 212 and Compound 211.

Figure 1B:
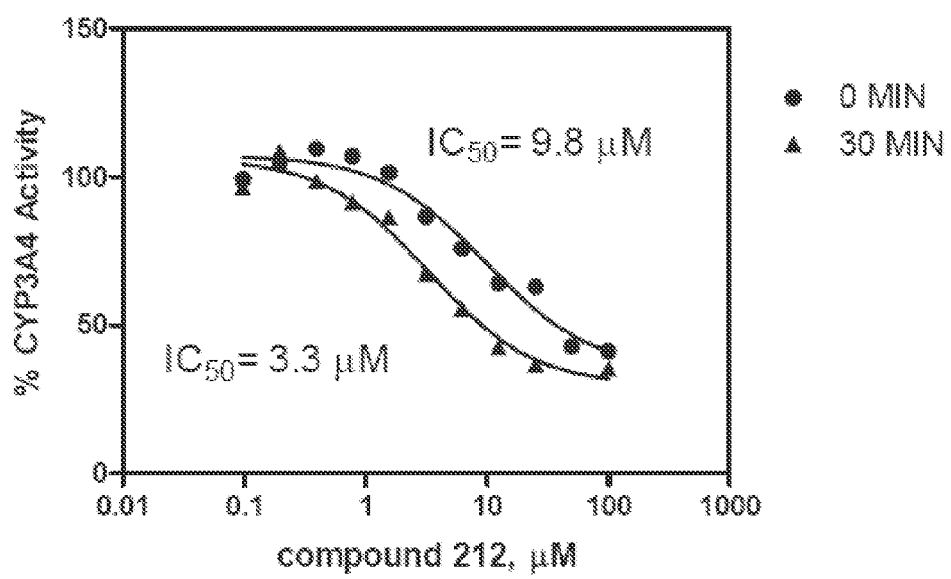
FIG. 1B shows $IC_{50}$ shift assessment plot for Compound 212.
Figure 1C:
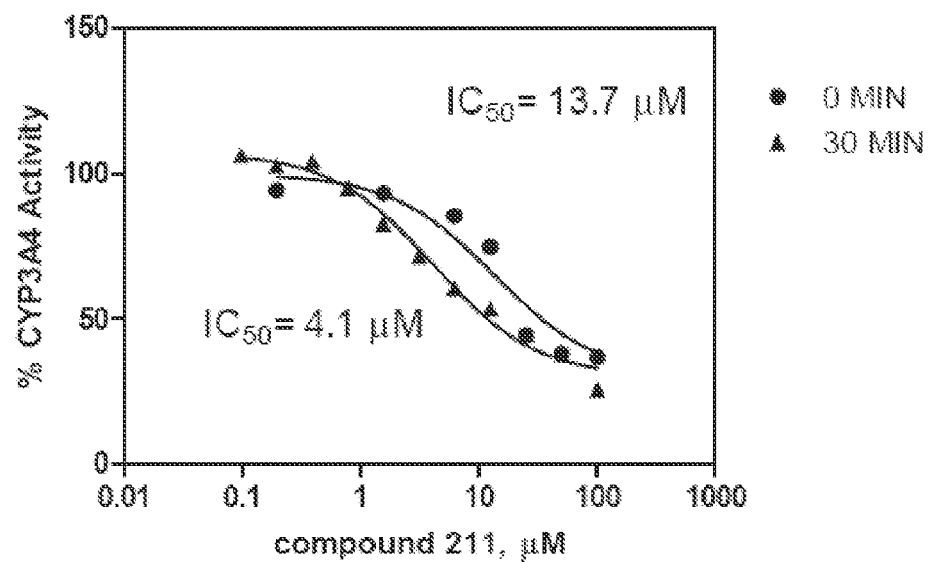
FIG. 1C shows $IC_{50}$ shift assessment plot for Compound 211.

The results of the Assessment of $IC_{50}$ Shift assays described above are shown in FIGS. 1A, 1B and 1C for each of the three compounds tested—crizotinib, Compound 212 and Compound 211, respectively. As is seen in the plots, the $IC_{50}$ shift for the metabolism of testosterone by CYP3A4 in the presence of crizotinib was 7.5-fold (from 11.2 to 1.5 μM). In contrast, the $IC_{50}$ shift for the metabolism of testosterone by CYP3A4 in the presence of compound 212 and of compound 211 was only 3.0-fold (from 9.8 to 3.3 μM) and 3.3-fold (from 13.7 to 4.1 μM), respectively. Accordingly, in the presence of either compound 212 or compound 211, metabolism of testosterone by CYP3A4 is shifted significantly less than in the presence of crizotinib.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:

1. A method of treating a disease or condition selected from lung cancer, non-small cell lung cancer, cutaneous or intraocular melanoma, colorectal cancer, colon cancer, gastric cancer, breast cancer, small intestinal cancer, cancer of the urethra, cancer of the prostate, lymphoma, sarcoma of soft tissue, cancer of the bladder, cancer of the kidney or ureter, renal cell carcinoma, neoplasms of the central nervous system (CNS), glioblastoma, brain stem glioma, neuroblastoma, pituitary adenoma, solid tumors or a combination of one or more of the foregoing cancers in a subject comprising the step of administering to the subject in need thereof a compound of Formula I:

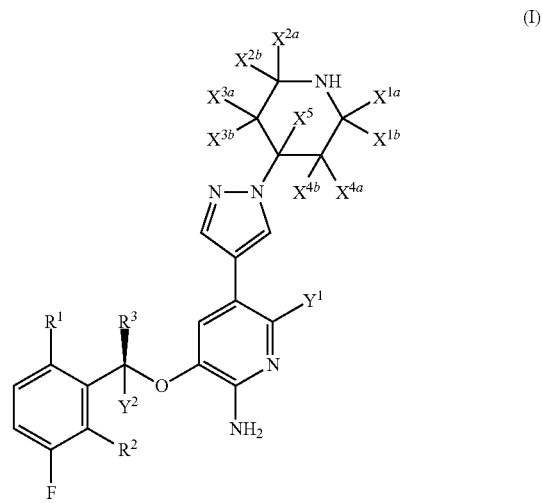

(I)

or a pharmaceutically acceptable salt thereof, wherein:
$R^1$ and $R^2$ are each Cl;
$R^3$ is $CH_3$ or $CD_3$;
$X^{1a}$, $X^{1b}$, $X^{2a}$ and $X^{2b}$ are the same and are hydrogen or deuterium;
$X^{3a}$, $X^{3b}$, $X^{4a}$ and $X^{4b}$ are the same and are hydrogen or deuterium;
$X^5$ is hydrogen or deuterium;
$Y^1$ is hydrogen or deuterium; and
$Y^2$ is hydrogen or deuterium;
provided that $X^{1a}$, $X^{1b}$, $X^{2a}$ and $X^{2b}$ are each deuterium, or $X^{3a}$, $X^{3b}$, $X^{4a}$ and $X^{4b}$ are each deuterium, or $X^{1a}$, $X^{1b}$, $X^{2a}$, $X^{2b}$, $X^{3a}$, $X^{3b}$, $X^{4a}$ and $X^{4b}$ are each deuterium, or a pharmaceutical composition comprising the compound of Formula I or a pharmaceutically acceptable salt thereof.

2. The method of claim 1, wherein the disease or condition is selected from non-small cell lung cancer (NSCLC), solid tumor cancer, neuroblastoma and lymphoma.

3. The method of claim 1, wherein the disease or condition is non-small cell lung cancer (NSCLC).

4. The method of claim 1, wherein for the compound of Formula I, deuterium incorporation at any atom designated as deuterium is at least 90%.

5. The method of claim 1, wherein for the compound of Formula I, deuterium incorporation at any atom designated as deuterium is at least 95%.

6. The method of claim 1, wherein for the compound of Formula I, deuterium incorporation at any atom designated as deuterium is at least 97%.

7. The method of claim 1, wherein the subject is positive for anaplastic lymphoma kinase (ALK).

8. The method of claim 3, wherein the subject is positive for anaplastic lymphoma kinase (ALK).

* * * * *